(12) United States Patent
Okamoto

(10) Patent No.: US 9,339,171 B2
(45) Date of Patent: May 17, 2016

(54) ENDOSCOPE

(71) Applicant: OLYMPUS CORPORATION, Tokyo (JP)

(72) Inventor: Yasuhiro Okamoto, Hino (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 13/791,962

(22) Filed: Mar. 9, 2013

(65) Prior Publication Data

US 2013/0267775 A1 Oct. 10, 2013

Related U.S. Application Data

(63) Continuation of application No. PCT/JP2012/073146, filed on Sep. 11, 2012.

(30) Foreign Application Priority Data

Sep. 26, 2011 (JP) .................. 2011-209367

(51) Int. Cl.
| | | |
|---|---|---|
| *A61B 1/005* | (2006.01) | |
| *A61B 1/05* | (2006.01) | |
| *G02B 23/24* | (2006.01) | |
| *A61B 1/00* | (2006.01) | |

(52) U.S. Cl.
CPC ............. *A61B 1/0052* (2013.01); *A61B 1/0016* (2013.01); *A61B 1/05* (2013.01); *G02B 23/2476* (2013.01)

(58) Field of Classification Search
CPC ................. A61B 17/07207; A61B 2017/2927; A61B 17/068
USPC ................................ 600/145, 146, 148, 149
See application file for complete search history.

(56) References Cited

U.S. PATENT DOCUMENTS

| 6,752,758 B2 * | 6/2004 | Motoki et al. ................. 600/146 |
| 2004/0193015 A1 | 9/2004 | Ikeda et al. |

(Continued)

FOREIGN PATENT DOCUMENTS

| JP | 2003-325437 | 11/2003 |
| JP | 2008-035882 | 2/2008 |

(Continued)

OTHER PUBLICATIONS

Extended Supplementary European Search Report dated Feb. 4, 2015 received in Application No. / Patent No. 12835763.9-1660.

*Primary Examiner* — John P Leubecker
*Assistant Examiner* — Rajaa El Alami
(74) *Attorney, Agent, or Firm* — Scully, Scott, Murphy & Presser, P.C.

(57) ABSTRACT

An endoscope includes: an operation portion provided on a proximal end side of an insertion portion; one pair of pulling members extending from a bending portion; a pulley rotated by a motor; rotating bodies that are elastically deformable and arranged on the pulley; a suspension frame to which the pulling members are fixed; a manipulator provided to project from the operation portion, the manipulator being capable of applying an amount of force of pulling a part of a pulling member on the insertion portion side using a frictional resistance generated as a result of, upon a tilting operation being performed, the pulling member being pulled to reduce a diameter of the corresponding rotating body and the rotating body being thereby brought into contact with the pulley; and a force amount adjustment section capable of changing the amount of force of pulling by making an adjustment of a friction generation state.

8 Claims, 19 Drawing Sheets

(56) References Cited

U.S. PATENT DOCUMENTS

2008/0275302 A1* 11/2008 Hosaka ..................... 600/139
2009/0076330 A1   3/2009 Ashida
2011/0009698 A1*  1/2011 Ashida et al. ............... 600/118

FOREIGN PATENT DOCUMENTS

| JP | 2009-005836 | 1/2009 |
| JP | 2011-019548 | 2/2011 |

* cited by examiner

| SHAFT PORTION TILTING ANGLE | UPWARD BENDING ANGLE | MOTOR ROTATION SPEED |
|---|---|---|
| 0 TO 10 DEGREES | 0 TO 30 DEGREES | 1 TIMES |
| 10 TO 20 DEGREES | 30 TO 60 DEGREES | 1.1 TIMES |
| 20 TO 30 DEGREES | 60 TO 90 DEGREES | 1.2 TIMES |
| 30 TO 40 DEGREES | 90 TO 120 DEGREES | 1.3 TIMES |
| 40 DEGREES OR MORE | 120 DEGREES OR MORE | 1.5 TIMES |

ENDOSCOPE

CROSS REFERENCE TO RELATED APPLICATION

This application is a continuation application of PCT/JP2012/073146 filed on Sep. 11, 2012 and claims benefit of Japanese Application No. 2011-209367 filed in Japan on Sep. 26, 2011, the entire contents of which are incorporated herein by this reference.

BACKGROUND OF THE INVENTION

1. Field of the Invention

The present invention relates to an endoscope that changes a tilting direction and a tilting angle of a manipulator provided at an operation portion to move a pulling member, thereby performing an operation to bend a bending portion provided in an insertion portion.

2. Description of the Related Art

In recent years, in a medical field and an industrial field, endoscopes including an elongated insertion portion have been used. With the endoscopes in the medical field, the insertion portion is inserted into a body from, e.g., an oral cavity or an anus to perform, e.g., observation. On the other hand, with the endoscopes in the industrial field, the insertion portion is inserted into, e.g., a piping of a boiler or an inner portion of an engine to perform observation.

In such endoscopes, a bending portion that bends, e.g., upward, downward, rightward and leftward is provided on the distal end side of the insertion portion. The endoscopes provided with the bending portion enable an observation optical system provided in a distal end portion to be directed to a desired direction by performing an operation to bend the bending portion.

In an operation portion provided on the proximal end side of the insertion portion including the bending portion, a bending knob for performing an operation to bend the bending portion, for example, upward/downward or leftward/rightward is pivotably provided. Respective one ends of bending wires corresponding to the respective bending directions are joined to predetermined positions in the bending portion and the respective other ends of the bending wires are joined to the bending knob.

With an endoscope with such configuration, an operator arbitrarily rotates the bending knob clockwise or counterclockwise by the fingers of the hand grasping the operation portion, to pull or loosen the joined bending wires, whereby the bending portion is bent. In recent years, there have been proposed endoscopes provided with drive means inside the operation portion of the respective endoscope, in which bending wires are pulled or loosened by operating a manipulator, which is a bending mechanism, by the fingers, enabling the bending portion to be bent in a desired direction.

In the endoscope according to Japanese Patent Application Laid-Open Publication No. 2003-325437, respective bending wires are wound and arranged in advance on a pulley that rotates by means of a motor, which is drive means, in a predetermined loosened state. When an operator performs an operation to bend the bending portion, the operator performs an operation to tilt an operation instruction lever (corresponding to a manipulator in the present description), which is a manipulator. Then, a bending wire corresponding to the tilting direction of the operation instruction lever is pulled and brought into contact with the pulley. Then, a resistive force between the bending wire and the pulley increases, whereby the wire is moved in a rotation direction of the pulley and the bending portion is bent in a desired direction.

In other words, in the endoscope described above, a bending wire pulling force amount for moving the bending wire can be obtained by the rotating pulley to perform an operation to bend the bending portion. In other words, the following equation can be provided:

Bending wire pulling force amount=Operation instruction lever tilting operation force amount+ Assist force amount.

With an endoscope with such configuration, an operation force amount for performing an operation to tilt an operation instruction lever can be reduced to reduce the burden of an operator.

Here, "assist force amount" refers to auxiliary power for moving a bending wire, which can be obtained from a rotating pulley.

Also, Japanese Patent Application Laid-Open Publication No. 2009-5836 indicates an endoscope including a pulling member operation apparatus according to above-mentioned Japanese Patent Application Laid-Open Publication No. 2003-325437, the endoscope including a bending mechanism enabling a bending portion to be bent efficiently relative to an amount of pulling a pulling member by an operation portion, without an increase in size of an operation portion.

SUMMARY OF THE INVENTION

An endoscope according to an aspect of the present invention includes an operation portion provided on a proximal end side of an insertion portion that includes a distal end portion including an image pickup device that picks up an image of an object, a bendable bending portion including a plurality of bending pieces continuously provided and a flexible tube portion that is elongated and has flexibility, the distal end portion, the bending portion and the flexible tube portion being continuously provided; at least one pair of pulling members that extend from the bending pieces included in the bending portion, are guided into the operation portion and bend the bending portion by a relative movement; a pulley provided inside the operation portion, the pulley being rotated by a motor provided in the operation portion in a pulling direction in which any of the pulling members is pulled; rotating bodies that are elastically deformable, each including an outer circumferential face with the respective pulling members wound and arranged thereon, the rotating bodies being arranged in a loose-fit state on an outer circumferential face side of the pulley; a suspension frame including attachment portions to which the at least one pair of pulling members guided into the operation portion are respectively fixed; a manipulator that is provided so as to project from a surface of the operation portion and includes a shaft portion capable of being subjected to a tilting operation, the suspension frame being provided at the shaft portion of the manipulator, the attachment portions of the suspension frame being provided at positions facing each other across the manipulator, the manipulator being capable of applying an amount of force of pulling a part of a pulling member on the insertion portion side relative to the pulley in the pulling direction using a frictional resistance generated as a result of, upon an operation to tilt the manipulator being performed, a part of the pulling member on the manipulator side relative to the pulley being pulled to reduce a diameter of the corresponding rotating body and an inner surface of the rotating body being thereby brought into contact with an outer circumferential face of the pulley rotated by the motor; and a force amount adjustment section capable of changing the amount of force of pulling the part of the pulling member on the insertion portion side relative to the pulley by making an adjustment of a friction generation state in which the frictional resistance is generated along with the tilting of the manipulator.

BRIEF DESCRIPTION OF THE DRAWINGS

FIGS. 1 to 10 are diagrams relating to a first embodiment of the present invention, and FIG. 1 is a diagram illustrating an endoscope in which a manipulator, which is included in a pulling member operation apparatus, is provided in a standing manner in an operation portion;

FIG. 2 is a block diagram illustrating a configuration of an endoscope with a pulling member operation apparatus incorporated in an operation portion;

FIG. 3 is a diagram illustrating an example configuration of a rotating body to be arranged on a pulley;

FIG. 4 is an example of table data, and is a diagram illustrating a state of settings for the shaft portion tilting angle of a manipulator and the motor rotation speed;

FIG. 5 is a diagram illustrating a relationship between the bending angle of a bending portion and the assist force amount;

FIG. 6 is a diagram illustrating a relationship between the bending angle of the bending portion and the tilting operation force amount of the manipulator;

FIG. 7 is a diagram illustrating an example configuration of an endoscope system including a switch for setting an initial rotation speed of a motor in a bending control apparatus or a switch for selecting one from a plurality of pieces of table data registered in a storage section and setting the selected table data;

FIG. 8 is a diagram illustrating a relationship between the bending angle of the bending portion and the manipulator tilting operation force amount for each of the table data registered in the storage section;

FIG. 10 is a diagram illustrating, e.g., a normal force of a rotating body with an inner surface having a uniform friction coefficient;

FIG. 11 is a diagram illustrating an endoscope having a characteristic in a pulley in a pulling member operation apparatus arranged in an operation portion;

FIG. 12 is a diagram of an outer appearance of the pulley:

FIG. 13 is a schematic cross-sectional diagram illustrating a configuration of the pulley;

FIG. 14 is a cross-sectional view of Y14-Y14 in FIG. 13;

FIG. 15 is a cross-sectional view of Y15-Y15 in FIG. 13;

FIG. 16 is a diagram illustrating an operation of the pulley;

FIG. 19A is a diagram illustrating a pulley arrangement position in which a moving stick is arranged at a first position and an assist force amount is smallest among three levels;

FIG. 19B is a diagram illustrating a pulley arrangement position in which a moving stick is arranged at a second position and an assist force amount is intermediate among three levels;

FIG. 19C is a diagram illustrating a pulley arrangement position in which a moving stick is arranged at a third position and an assist force amount is largest among three levels;

FIG. 20 is a diagram illustrating a pulley including a second pulley portion in an operation portion, the second pulley portion being a replaceable one;

FIG. 21 is a diagram illustrating an attachment;

FIG. 22 is a diagram illustrating a manner of replacement of the second pulley portion in the pulley in FIG. 20;

FIG. 23 is a diagram illustrating a pulley including a pulley portion and an operation lever;

FIG. 24 is a diagram illustrating the operation lever; and

FIG. 25 is a diagram illustrating an operation of the pulley in FIG. 23.

DETAILED DESCRIPTION OF THE PREFERRED EMBODIMENTS

Embodiments of the present invention will be described below with reference to the drawings.

A first embodiment of the present invention will be described with reference to FIGS. 1 to 10.

Figure 1:
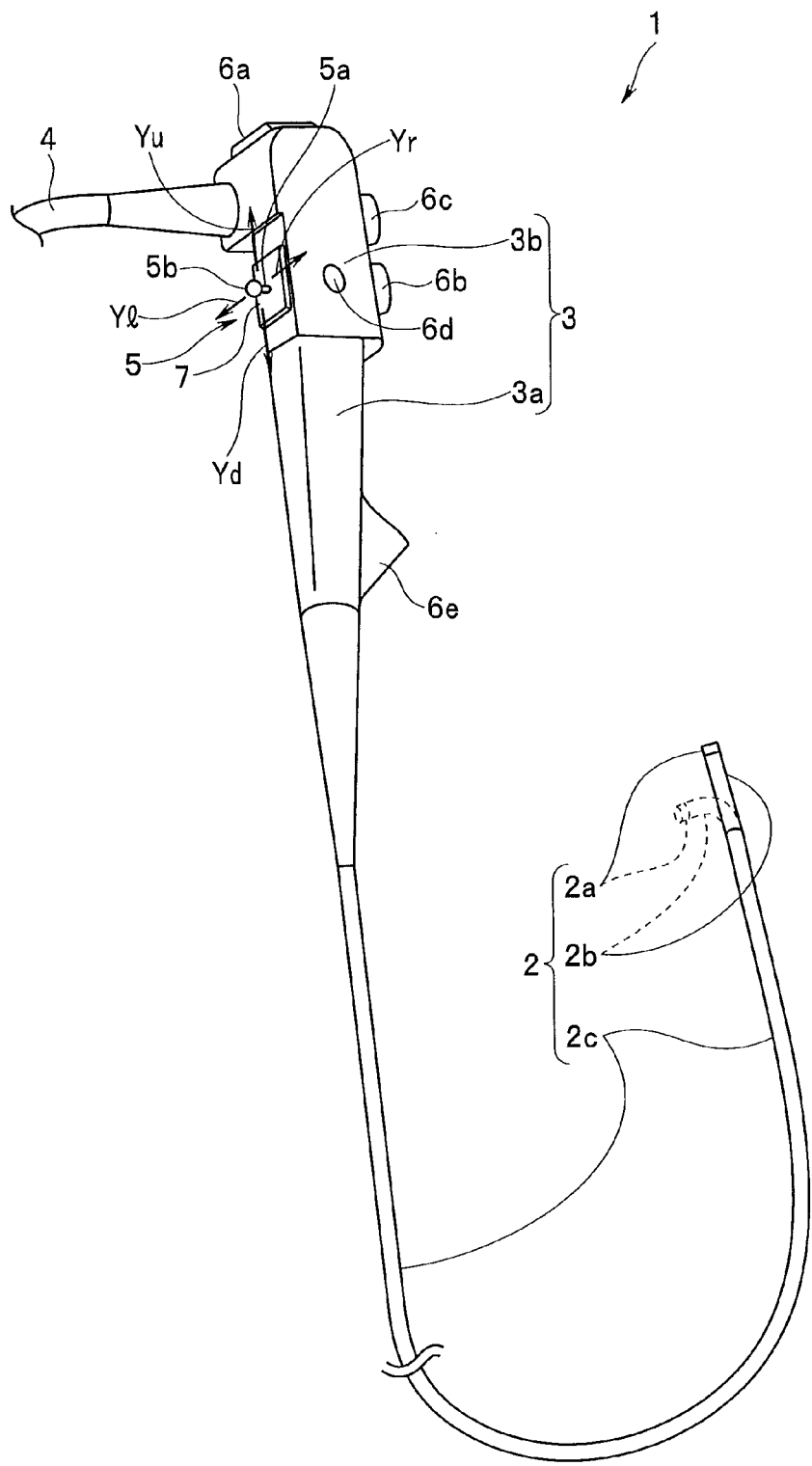
Figure 2:
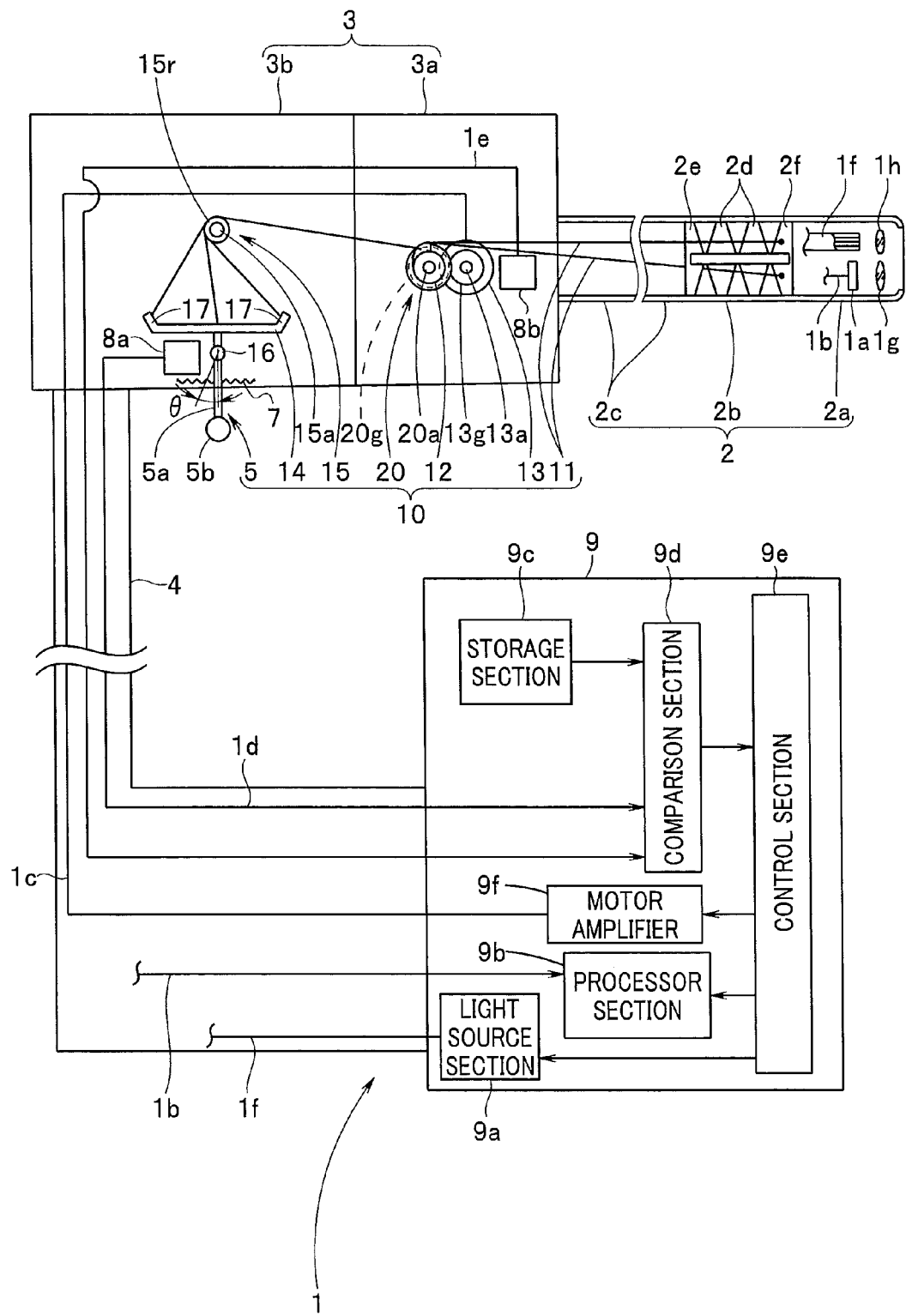

As illustrated in FIGS. 1 and 2, an endoscope 1 according to the present embodiment includes an elongated insertion portion 2, an operation portion 3 and a universal cord 4. The operation portion 3 is provided so as to be continuous with a proximal end of the insertion portion 2. The universal cord 4 extends from a side portion of the operation portion 3. A proximal end of the universal cord 4 is joined to a bending control apparatus 9, which is an apparatus external to the endoscope 1.

The insertion portion 2 includes a distal end portion 2a, a bending portion 2b and a flexible tube portion 2c continuously provided in this order from the distal end side. The flexible tube portion 2c has flexibility and has a long length. In the distal end portion 2a, an image pickup apparatus 1a including an image pickup device is incorporated.

The operation portion 3 includes a grasping portion 3a and an operation portion body 3b. The grasping portion 3a is provided so as to be continuous with the insertion portion 2, and the operation portion body 3b is provided so as to be continuous with the grasping portion 3a. As illustrated in FIG. 2, a pulling member operation apparatus 10 is provided inside the operation portion 3. In the present embodiment, a longitudinal axis of the grasping portion 3a and an insertion axis of the insertion portion 2 are in a positional relationship in which the longitudinal axis and the insertion axis are coaxial or parallel to each other. Also, a longitudinal axis of the operation portion body 3b and the longitudinal axis of the grasping portion 3a are in a positional relationship in which the longitudinal axes are coaxial or parallel to each other.

Inside an empty space in the operation portion body 3b, a manipulator 5 is provided. The manipulator 5 is operated when an operation to bend the bending portion 2b is performed. The manipulator 5 projects from a manipulator projection port (not illustrated). The manipulator projection port is an opening and is formed in a surface provided in the operation portion body 3b, the surface being parallel to the longitudinal axis. A shaft portion 5a of the manipulator 5 is arranged orthogonal to the longitudinal axis when the bending portion 2b is linear. Reference numeral 5b denotes a finger rest portion, which is provided at an end portion of the shaft portion 5a.

The bending portion 2b is configured so as to include a plurality of bending pieces 2d provided continuously and be bendable in, for example, four directions, upward, rightward, downward and leftward. Reference numeral 2e denotes a proximal end bending piece. The proximal end bending piece 2e provides a proximal end of the bending portion 2b and is joined to the distal end side of the flexible tube portion 2c. Reference numeral 2f denotes a distal end bending piece. The distal end bending piece 2f provides a distal end of the bending portion 2b and is joined to the proximal end side of the distal end portion 2a.

The bending portion 2b bends, e.g., upward, rightward, downward or leftward or in a direction between the upper direction and the right direction according to a tilting operation including a tilting direction and a tilting angle of the manipulator 5. More specifically, the bending portion 2b bends upward upon the manipulator 5 being tilted in the arrow Yu direction in FIG. 1, bends downward upon the manipulator 5 being tilted in the arrow Yd direction, bends leftward upon the manipulator 5 being tilted in the arrow Yl direction, and bends rightward upon the manipulator 5 being tilted in the arrow Yr direction.

Note that, in the present embodiment, the bending portion 2b is configured to bend in four directions, i.e., upward, downward, leftward and rightward. However, the bending portion 2b may be configured to bend in two directions, i.e., upward and downward.

In the sheath of the operation portion body 3b, a switch 6a, an air/water feeding button 6b and a suction button 6c are provided at predetermined positions in addition to the manipulator 5. The switch 6a is, for example, a switch for giving instructions to perform various image pickup operations of the image pickup apparatus 1a provided inside the distal end portion 2a.

As illustrated in FIG. 2, inside the universal cord 4, e.g., an image pickup cable 1b, a motor cable 1c, an angle sensor cable 1d, a speed sensor cable 1e, a light guide fiber bundle 1f, an air feeding tube (not illustrated), a water feeding tube (not illustrated) and a suction tube (not illustrated) are inserted. The image pickup cable 1b is connected to the image pickup apparatus 1a. The motor cable 1c is connected to a motor 13, which will be described later. The angle sensor cable 1d is connected to a tilting angle detection sensor 8a. The speed sensor cable 1e is connected to a motor rotation speed detection sensor 8b. The light guide fiber bundle 1f conveys illuminating light from a light source section 9a.

In FIG. 2, reference numeral 1g denotes an objective optical system, and reference numeral 1h denotes an illumination window. Illuminating light exiting from the light guide fiber bundle 1f passes through the illumination window 1h and exits toward a site to be observed. An observation image of the site to be observed, which is illuminated with the illuminating light, passes through the objective optical system 1g and is formed on an image pickup surface of the image pickup device.

Reference numeral 6d in FIG. 1 denotes a cap body, which will be described later. Reference numeral 7 in FIGS. 1 and 2 denotes a cover member. The cover member 7 occludes the manipulator projection port in a watertight manner and is in close contact with the shaft portion 5a to hold the manipulator 5 in such a manner that the manipulator 5 can be tilted. In the sheath of the grasping portion 3a, a channel insertion opening 6e that is in communication with a treatment instrument channel (not illustrated) is provided.

As illustrated in FIG. 2, the pulling member operation apparatus 10 mainly includes bending wires 11, an elongated pulley 20, the motor 13, a suspension frame 14, the manipulator 5 and a guide roller 15. The bending wires 11 are pulling members. In the elongated pulley 20, a plurality of rotating bodies 12 are disposed. The motor 13 rotates the pulley 20. The suspension frame 14 has a substantial cruciform. The manipulator 5 is fixed to the suspension frame 14 in an integrated manner.

In the present embodiment, for example, a motor shaft 13a of the motor 13, a pulley shaft 20a of the pulley 20 and a roller shaft 15a of the guide roller 15 are set to have a positional relationship in which the motor shaft 13a, the pulley shaft 20a and the roller shaft 15a are parallel to one another.

The bending wires 11 are provided so as to correspond to bending directions of the bending portion 2b. In the present embodiment, the bending wires 11 include four wires, i.e., an upward bending wire, a downward bending wire, a leftward bending wire and a rightward bending wire.

The rotating bodies 12 are provided so as to correspond to the respective bending wires 11. In the present embodiment, the rotating bodies 12 include four rotating bodies, i.e., a rotating body for upward bending, a rotating body for downward bending, a rotating body for leftward bending and a rotating body for leftward bending. An intermediate portion of the upward bending wire is wound on an outer circumferential face of the rotating body 12 for upward bending. An intermediate portion of the downward bending wire is wound on an outer circumferential face of the rotating body 12 for downward bending. An intermediate portion of the leftward bending wire is wound on an outer circumferential face of the rotating body 12 for leftward bending. An intermediate portion of the rightward bending wire is wound on an outer circumferential face of the rotating body 12 for rightward bending.

Figures 3, 4:
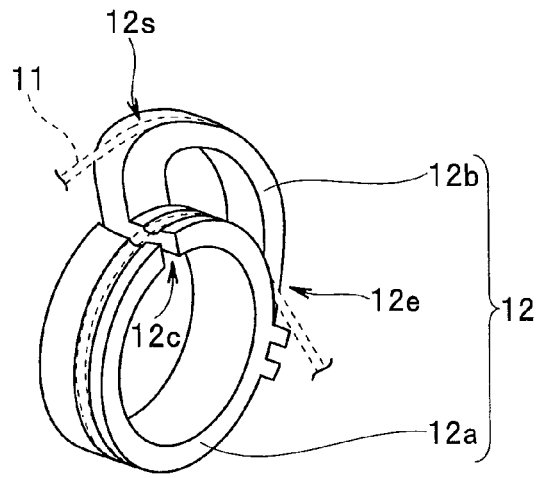

The rotating bodies 12 are elastically deformable. As illustrated in FIG. 3, each rotating body 12 includes an annular portion 12a, and a rotation amount adjustment portion 12b, and in the annular portion 12a, a gap 12c is formed. In the annular portion 12a and the rotation amount adjustment portion 12b, a wire guiding portion is formed. The wire guiding portion is configured to have a predetermined shape so as to smoothly guide the corresponding bending wire 11 from a winding start position 12s to a winding end position 12e.

The four rotating bodies 12 are arranged in a predetermined loose-fit state on an outer circumferential face of the pulley 20. Ordinarily, the respective rotating bodies 12 are configured to enter a rotating state independently from the pulley 20. A pulley-side gear 20g is fixed to the pulley shaft 20a of the pulley 20.

Note that the rotating bodies 12 are not limited to ones having the shape including the annular portion 12a and the rotation amount adjustment portion 12b, and may have, for example, what is called a C-ring shape, which is an annular portion 12a including a gap 12c.

The motor 13 is drive means for, during a bending operation, rotating a rotating body 12 according to the bending direction, provided on the pulley 20, with a predetermined torque. A motor-side gear 13g is fixed to the motor shaft 13a of the motor 13. The motor-side gear 13g engages with the pulley-side gear 20g.

Accordingly, a driving force from the motor 13 is transmitted to the pulley 20 via the motor-side gear 13g fixed to the motor shaft 13a and the pulley-side gear 20g fixed to the pulley shaft 20a.

A rotation frequency of the motor 13 in the present embodiment is set according to a control signal outputted from a motor amplifier 9f. The motor 13 is set in advance so as to operate at a rotation speed V (rotation frequency N) in an initial state (at the time of power-on).

The substantially-cruciform suspension frame 14 includes wire attachment portions 17. Proximal ends of the respective wires 11 are joined to the respective wire attachment portions 17.

The guide roller 15 is a wire running route changing member that changes routes on which the wires 11 run inside the operation portion 3. The guide roller 15 is arranged at a predetermined position relative to the suspension frame 14. The guide roller 15 includes the roller shaft 15a and four guide rollers 15r pivotably arranged on the roller shaft 15a.

The tilting angle detection sensor (hereinafter abbreviated as angle sensor) 8a is a tilting operation angle detection apparatus such as an encoder and is included in a force amount adjustment section. The angle sensor 8a detects a tilting angle of the shaft portion 5a of the manipulator 5. A result of detection by the angle sensor 8a is tilting angle information and is outputted to the bending control apparatus 9 via the angle sensor cable 1d.

The speed sensor 8b is a motor rotation state detection apparatus and is included in the force amount adjustment section. The speed sensor 8b detects a rotation speed of the motor 13. A result of detection by the speed sensor 8b is rotation speed information and is outputted to the bending control apparatus 9 via the speed sensor cable 1e.

Note that the motor rotation state detection apparatus may be a motor rotation frequency detection sensor that detects a rotation frequency of the motor instead of the motor rotation speed detection sensor 8b. Reference numeral 16 denotes a universal joint and is pivotally disposed in a non-illustrated frame.

The shaft portion 5a of the manipulator 5 and a frame projection portion, which is a center axis of the suspension frame 14, are concentrically attached and fixed to each other via the universal joint 16. The bending wires 11 are inserted inside a guide pipe (see reference numeral 18 in FIG. 11), which is a metal coil pipe, inside the insertion portion 2 and extends out to the distal end portion side. End portions of the respective bending wires 11 are fixed at respective positions of the distal end bending piece 2f that correspond to upward, downward, leftward and rightward bending.

The bending control apparatus 9 mainly includes, for example, a light source section 9a, a processor section 9b, a storage section 9c, a comparison section 9d and a control section 9e.

The light source section 9a includes, e.g., an LED (not illustrated) or a lamp (not illustrated) that supplies illuminating light to the light guide fiber bundle 1f. The processor section 9b outputs a signal for driving the image pickup device via the image pickup cable 1b, and also, upon receipt of a signal photoelectrically converted by the image pickup device, generates a video signal and outputs the video signal to a non-illustrated display apparatus.

Note that, in the embodiment, the bending control apparatus 9 is configured to include the light source section 9a and the processor section 9b. However, a configuration in which the light source section 9a is a light source apparatus, which is an apparatus external to the endoscope 1, and the processor section 9b is a video processor, which is an external apparatus, whereby the light source section 9a and the processor section 9b are separately provided, may be employed.

Also, a configuration in which a light-emitting device such as an LED is arranged in a distal end portion instead of provision of the light guide fiber bundle if may be employed.

The storage section 9c, the comparison section 9d and the control section 9e are included in the force amount adjustment section.

In the storage section 9c, table data in which a relationship between a tilting angle of the shaft portion 5a of the manipulator 5, for example, an upward bending angle for the tilting angle and a motor rotation speed corresponding to the tilting angle is set is registered. As illustrated in FIG. 4, the table data is set so that the rotation frequency increases at, for example, a predetermined ratio with reference to a rotation speed from a state where the tilting angle of the shaft portion 5a is 0 degrees (perpendicular to the surface) to a state where an angle θ in FIG. 2 is, for example, 10 degrees.

A tilting angle of the shaft portion 5a detected by the angle sensor 8a and a rotation speed of the motor 13 detected by the speed sensor 8b are inputted to the comparison section 9d. Then, the comparison section 9d compares the inputted tilting angle of the shaft portion 5a and the inputted rotation speed of the motor 13, and the table data registered in the storage section 9c. The comparison section 9d outputs a result of the comparison to the control section 9e as motor control information.

The control section 9e performs control of the rotation frequency of the motor 13 based on the motor control information inputted from the comparison section 9d in addition to the above-described control of the light source section 9a and the processor section 9b. Where, for example, the tilting angle of the shaft portion 5a is 15 degrees, the control section 9e rotates the motor 13 at a rotation speed 1.1 times higher than an initial rotation speed. As a result, the rotation frequency of the motor 13 is increased to a predetermined value.

Note that the relationship between an tilting angle of the shaft portion 5a of the manipulator 5 and the motor speed corresponding to the tilting angle is not limited to the relationship illustrated in FIG. 4. In other words, settings may arbitrarily be made so that along with a change in tilting angle of the shaft portion 5a of the manipulator 5, the rotation frequency of the motor 13 is linearly changed or exponentially changed, or linearly changed up to a predetermined inclination angle and then exponentially changed after the predetermined tilting angle onwards.

Here, a relationship between a motor speed, a bending portion bending angle and an assist force amount will be described.

Note that, as described above, among an assist force amount, a bending wire pulling force amount and an operation instruction lever tilting operation force amount, there is the following relationship:

Bending wire pulling force amount=Operation instruction lever tilting operation force amount+ Assist force amount.

Figure 5:
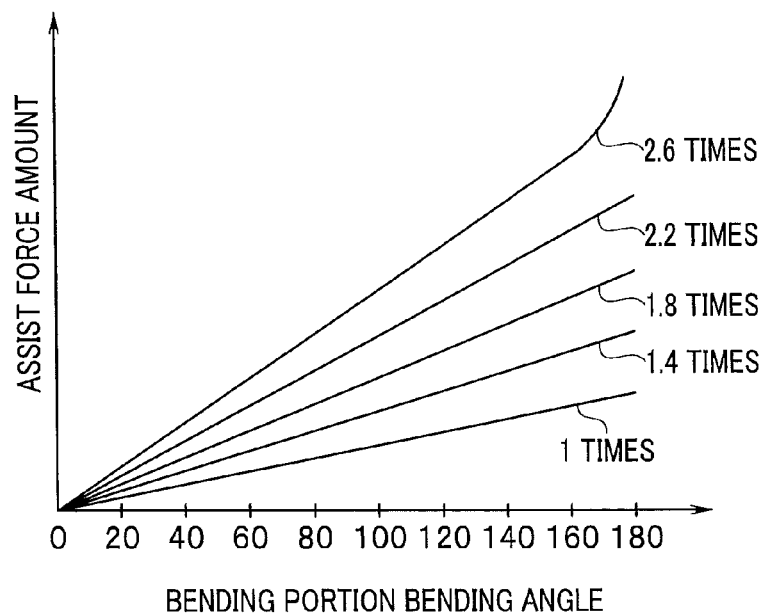

In order to verify the relationship between a rotation speed of the motor 13 and an assist force amount, a relationship between an upward bending portion bending angle and an assist force amount was confirmed with the rotation speed of the motor 13 changed to 1 time, 1.4 times, 1.8 times, 2.2 times and 2.6 times relative to the rotation speed in an initial state. As a result, as illustrated in FIG. 5, it has been confirmed that as the rotation speed of the motor 13 is higher, an increase in assist force amount along with an increase in bending angle of the bending portion is larger.

This is because along with an increase in rotation speed of the motor 13, rotation speeds of the pulley 20 and the rotating bodies 12 increase. Then, the pulley 20 and the rotating bodies 12 generate heat, whereby a temperature of the pulley 20 and temperatures of the rotating bodies 12 increase. Hardnesses of the pulley 20 and the rotating bodies 12 decrease along with the increase in temperature, whereby the area of contact between the pulley 20 and the rotating bodies 12 increases. Then, a friction force between the pulley 20 and the rotating bodies 12 increases, whereby slippage of the rotating bodies 12 relative to the pulley 20 is reduced. As a result, parts of the bending wires 11 arranged on the insertion portion 2 side relative to the rotating bodies 12 are more efficiently pulled along with rotation of the pulley 20.

Figure 6:
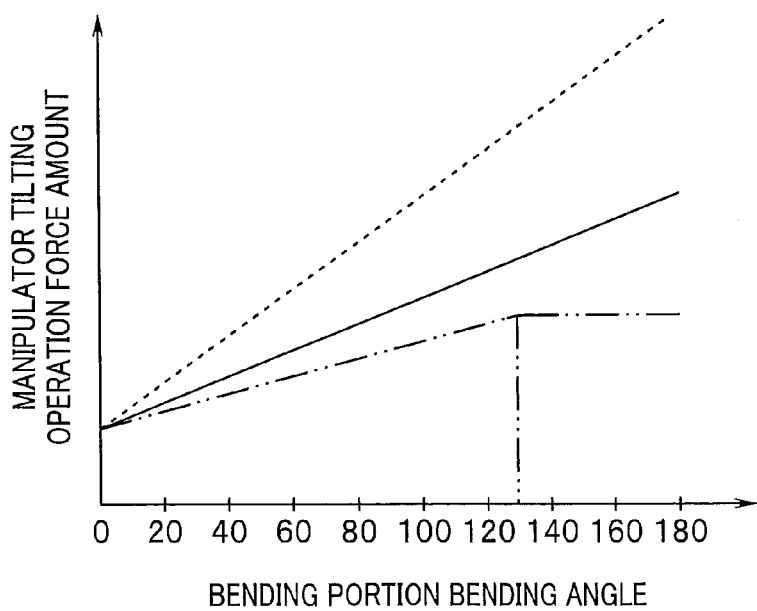

In other words, in the endoscope 1 in which the motor 13 rotates constantly at a rotation speed (one times) in an initial state, when an operation to tilt the manipulator 5 is performed to increase the bending angle of the bending portion 2b, as indicated by the dashed line in FIG. 6, as the bending angle is larger, the operation instruction lever tilting operation force amount substantially increases compared to that at the time of the start of the tilting.

On the other hand, in the endoscope 1 in which the bending angle of the bending portion 2b and the rotation speed of the motor 13 are set as indicated in the table data in FIG. 4, when an operation to tilt the manipulator 5 is performed to increase the bending angle of the bending portion 2b, as indicated by the solid line in FIG. 6, a decrease in operation instruction lever tilting operation force amount can be made.

Then, creation of new table data makes it possible to, e.g., when an operation to tilt the manipulator 5 is performed to increase the bending angle of the bending portion 2b, as indicated by the alternate long and two short dashes line in FIG. 6, makes the operation instruction lever tilting operation force amount be substantially constant after the bending angle of the bending portion exceeds a predetermined angle.

Here, an operation of an endoscope system including the endoscope 1 and the bending control apparatus 9 will be described.

With the endoscope 1 configured as described above, when the motor 13 is driven to rotate the pulley 20, if the shaft portion 5a of the manipulator 5 is in a standing state, the respective bending wires 11 wound on the four rotating bodies 12 corresponding to the upward, downward, leftward and rightward directions, which are arranged on the pulley 20, are all in a predetermined loosened state. As a result, all of the rotating bodies 12 slip on the pulley 20, whereby the bending portion 2b is held in a linear state.

On the other hand, an operator performs an operation to bend the bending portion 2b, for example, upward. In this case, the operator places the ball of his/her thumb on the finger rest portion 5b of the manipulator 5 with grasping the grasping portion 3a and performs an operation to tilt the shaft portion 5a in the arrow Yu direction in FIG. 1. Then, along with the tilting operation of the manipulator 5, the suspension frame 14 inclines. As a result, the upward bending wire 11 fixed to the wire attachment portion 17 for upward bending gradually changes from a loosened state to a pulled state, and the other bending wires 11 change to a further loosened state.

Then, from among the respective bending wires 11 wound in a loosened state on the four rotating bodies 12 on the pulley 20, only the upward bending wire 11 is pulled. Then, the gap 12c in the rotating body 12 for upward bending is narrowed against an elastic force, resulting in a decrease in a diameter of the rotating body 12 for upward bending, whereby the rotating body 12 for upward bending and the pulley 20 come into close contact with each other. As a result, a frictional resistance is generated between the rotating body 12 for upward bending and the pulley 20, whereby the rotating body 12 for upward bending rotates in a direction that is the same as a rotation direction of the pulley 20. Along with the rotation of the rotating body 12 for upward bending, the part of the upward bending wire 11 arranged on the insertion portion 2 side relative to the rotating body 12 for upward bending is pulled and thereby moved, whereby the bending portion 2b starts an operation to bend upward.

As a result of the operator performing an operation to further tilt the shaft portion 5a in the same direction continuously from the start of the operation so as to bring the rotating body 12 for upward bending into close contact with the pulley 20, the friction force between the rotating body 12 for upward bending and the pulley 20 in a close contact state further increases. As a result, the part of the upward bending wire 11 positioned on the insertion portion 2 side relative to the rotating body 12 is further pulled and thereby moved, whereby the bending portion 2b further bends upward.

Then, as the motor 13 is being driven, rotation speed information on a rotation speed of the motor 13 detected by the speed sensor 8b is outputted to the comparison section 9d. Furthermore, as an operation to tilt the manipulator 5 is being performed, tilting angle information on a tilting angle of the shaft portion 5a detected by the angle sensor 8a is outputted to the comparison section 9d.

In other words, the comparison section 9d consistently compares the tilting angle of the shaft portion 5a and the rotation speed of the motor 13, which have been inputted as described above, and the table data registered in the storage section 9c. Here, if the rotation speed is a speed corresponding to the tilting angle, the comparison section 9d outputs motor control information for maintaining the rotation speed to the control section 9e. On the other hand, if the rotation speed is a rotation speed not corresponding to the tilting, the comparison section 9d outputs a change instruction signal to the control section 9e. The change instruction signal is motor control information for changing the rotation speed to a rotation speed corresponding to the tilting.

If the control section 9e receives the signal for maintaining the rotation speed from the comparison section 9d, the control section 9e maintains the driving state of the motor 13 as it is. On the other hand, if the control section 9e receives the change instruction signal from the comparison section 9d, the control section 9e controls the motor amplifier 9f to rotate the motor 13 at a rotation frequency corresponding to the change instruction signal.

Then, as the tilting angle of the shaft portion 5a becomes larger, the control section 9e raises the rotation speed of the motor 13. As a result, when the operator operates the manipulator 5 to perform an operation to increase the tilting operation angle of the manipulator 5, that is, an operation to increase the bending angle of the bending portion, the assist force amount increases along with the bending angle increase.

As described above, the angle sensor 8 that detects a tilting angle and the speed sensor 8b that detects a rotation speed of the motor 13 are provided in the pulling member operation apparatus 10 in the endoscope 1. Also, the storage section 9c with table data registered therein, the comparison section 9d that compares tilting angle information and rotation speed information, and values in the table data in the storage section 9c and outputs motor control information to the control section 9e, and the control section 9e that controls a rotation frequency of the motor 13 according to the motor control information are provided in the bending control apparatus 9.

Then, table data in which a relationship of, e.g., a rotation speed of the motor 13 increasing in a preset manner as the shaft portion tilting angle increases is set is registered in the storage section 9c.

As a result, even if the bending portion 2*b* is bent at a large bending angle exceeding, for example, 120 degrees, the operator can smoothly perform a tilting operation of the manipulator 5. In other words, even in a situation in which the tilting angle of the manipulator 5 is large, making it difficult to put some muscle on the finger that performs the operation, the operator can easily perform the operation to tilt the manipulator 5.

Note that, if an operator, for example, inserts a treatment instrument into the treatment instrument channel in the endoscope 1 in the middle of the above-described bending portion operation, the operator inserts the treatment instrument with the bending state of the bending portion 2*b* maintained. In such case, the operator maintains the bending state of the bending portion 2*b* while the tilting state of the manipulator 5 is maintained by the finger. However, the operation to maintain the tilting state of the manipulator 5 by the finger put a strain on the finger, which causes fatigue. Thus, for reduction of a strain on the finger, that is, reduction in fatigue, it is possible to increase the motor rotation frequency to increase the assist force amount.

In such case, for example, if a range of fluctuations in value of current flowing in the motor 13 remains within a threshold range stored in the storage section 9*c* for a certain time period or longer, the motor rotation frequency is increased to assist an operation force amount required to maintain the tilting state of the manipulator 5. In this case, a configuration may be formed so that if the bending angle of the bending portion 2*b* is larger than a threshold angle stored in the storage section 9*c*, whether or not the tilting state of the manipulator 5 is maintained is determined as describe above.

Alternatively, if a range of fluctuations in tilting angle of the shaft portion 5*a* detected by the angle sensor 8*a* remains within a threshold range stored in the storage section 9*c* for a certain time period or longer, the motor rotation frequency is increased to assist an operation force amount required to maintain the titling state of the manipulator 5. In such case, a configuration may be made so that if the tilting angle of the shaft portion 5*a* detected by the angle sensor 8*a* is larger than a threshold value stored in the storage section 9*c*, whether or not the tilting state of the manipulator 5 is maintained is determined as described above.

Figure 7:
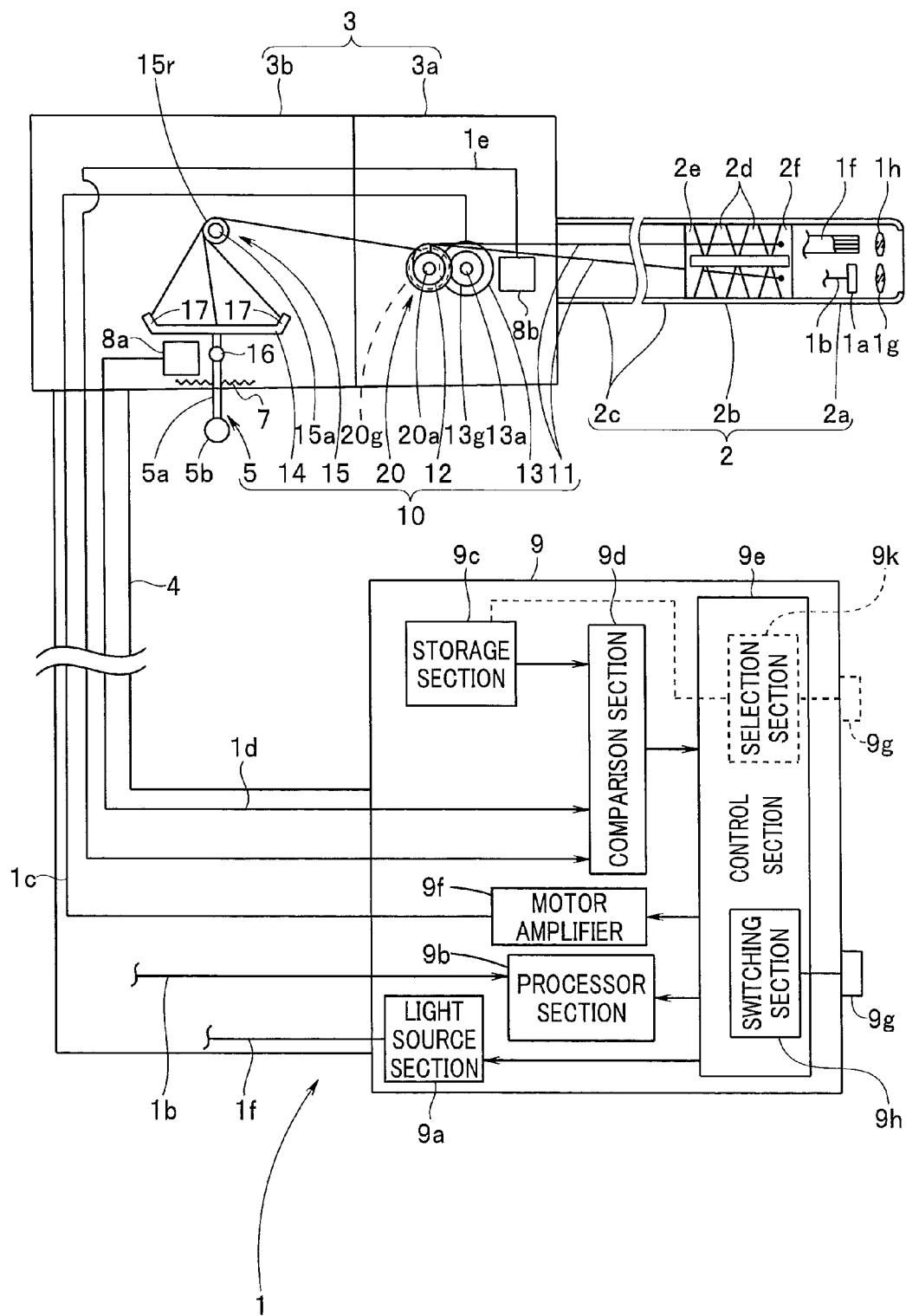

Also, for example, a first setting switch indicated by reference numeral 9*g* in FIG. 7 and a switching section 9*h* may be provided in the bending control apparatus 9. The first setting switch 9*g* is a switch for setting an initial rotation speed of the motor 13 via the switching section 9*h* in the control section 9*e*. The first setting switch 9*g* switches the initial rotation speed to, for example, 1.1 times, 1.2 times, 0.9 times or 0.8 times relative to the initial state each time a pushing operation is performed to change the setting. Note that the first setting switch 9*g* may be arranged at the operation portion 3.

As a result, an operator can easily change the setting of the initial rotation speed to a value different from the initial state to rotate the pulley 20, in order to perform an operation of the manipulator 5. With this configuration, if an operator wishes to perform an operation with a smaller amount of strength, the initial rotation speed is set to, for example, 1.2 times. Consequently, during a time period from a start of a tilting operation of the manipulator 5 until the bending portion 2*b* largely bends, the tilting operation can be performed with an optimum operational feeling.

Contrary to the above, if an operator wishes to perform an operation with a larger amount of strength, the initial rotation speed is set to, for example, 0.8 times. Consequently, during a time period from a start of the tilting operation of the manipulator 5 until the bending portion 2*b* largely bends, the tilting operation can be performed with an optimum operational feeling.

Also, instead of change of the setting of the initial rotation speed of the motor 13 being made via the first setting switch 9*g* provided in the bending control apparatus 9, a selection switch for selecting arbitrary table data from a plurality of pieces of table data stored in the storage section 9*c* may be provided. In this case, for example, a first selection switch 9*g* indicated by a dashed line in FIG. 7 and a selection section 9*k* are provided in the bending control apparatus 9. Also, as illustrated in FIG. 8, for example five pieces of table data d1, d2, d3, d4 and d5 set so that a manipulator tilting operation force amount changes according to the bending portion bending angle are registered in advance in the storage section 9*c*.

An operator selects desired table data from among the plurality of pieces of table data. As a result, during a time period from a start of a tilting operation of the manipulator 5 until the bending portion 2*b* largely bends, the operator can perform the tilting operation with an optimum operational feeling.

Figure 8:
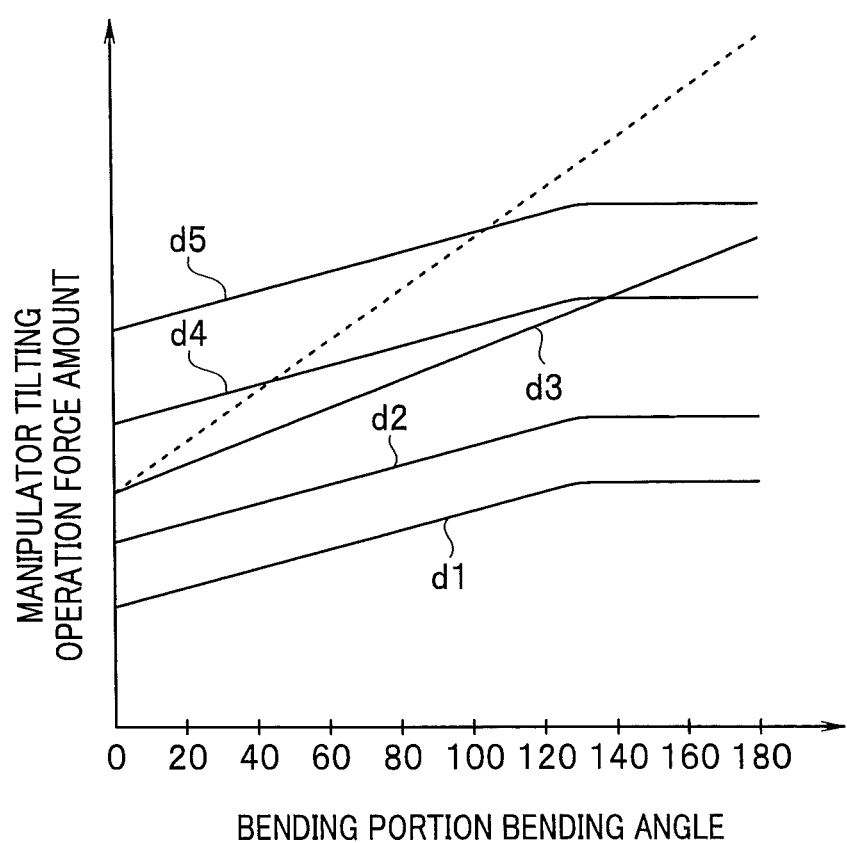

The straight line indicated by the dashed line in FIG. 8 indicates a relationship between the bending portion bending angle and the manipulator tilting operation force amount if the pulley is continuously rotated with the rotation speed of the motor 13 kept in an initial state. In this case, as described above, as the bending angle of the bending portion 2*b* becomes larger as a result of the operation to tilt the manipulator 5, the tilting operation force amount for the operation instruction lever substantially increases compared to that at the time of the start of tilting.

Also, in the above-described embodiment, the tilting angle of the shaft portion 5*a* of the manipulator 5 is measured to change the rotation speed of the motor 13. However, it is known that an increase in bending angle of the bending portion 2*b* increases a burden imposed on the motor 13, whereby the motor rotation frequency is lowered and the current value is increased. Thus, a configuration in which a current value detection apparatus that detects a current value of the motor 13 is provided instead of the angle sensor 8*a* and the rotation speed of the motor 13 is changed based on current detection information from the current value detection apparatus may be employed.

Note that, instead of measurement of the tilting angle of the shaft portion 5*a*, a C-ring rotation amount may be measured, a wire movement amount may be measured, or a wire tensile force may be measured, to change the rotation speed of the motor 13.

With such configuration, provision of the current value detection apparatus inside the bending control apparatus 9 enables elimination of the sensors from the operation portion 3 in the endoscope 1. The rest of the operation and effects is similar to those of the above-described embodiment.

Figure 9A:
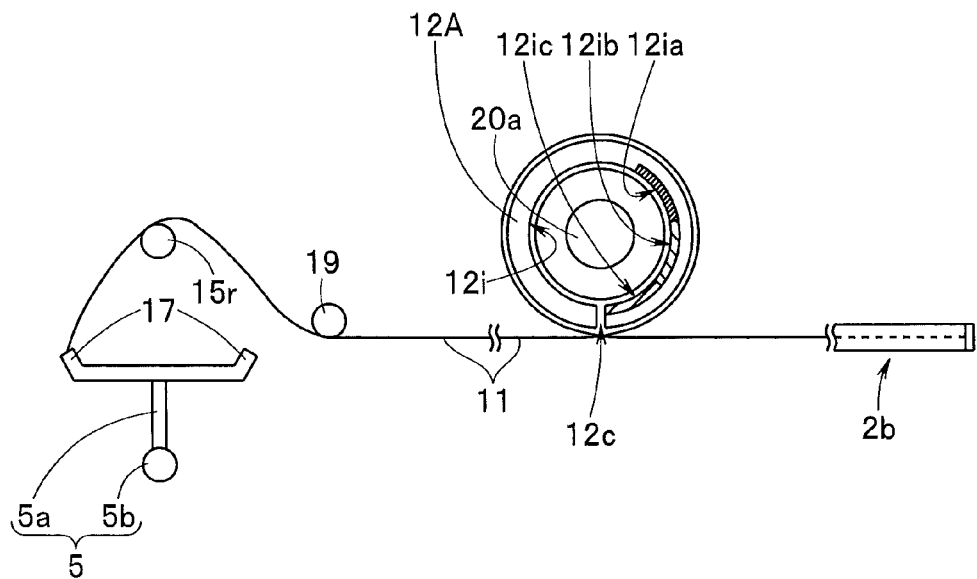
FIG. 9A is a diagram illustrating a rotating body with an inner surface whose friction coefficient is changed in a circumferential direction.
Figure 9B:
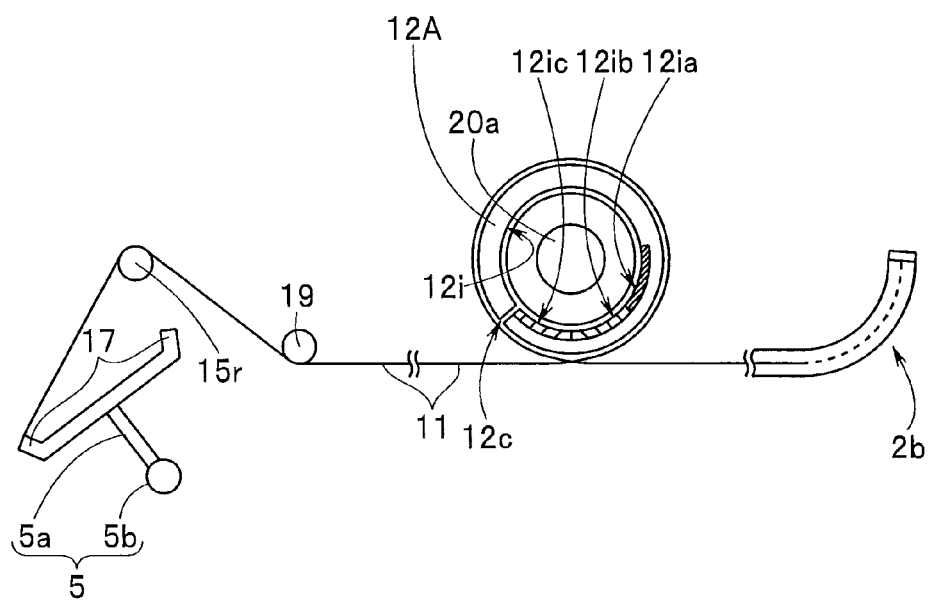
FIG. 9B is a diagram illustrating an operation of a rotating body with an inner surface whose friction coefficient varies in a circumferential direction.

In a rotating body 12A, which is illustrated in FIG. 9A, a friction coefficient of an inner surface 12*i* thereof changes in a stepwise manner in a circumferential direction within a predetermined range. More specifically, in the present embodiment, the friction coefficient of the inner surface 12*i* of the rotating body 12A is different among a first inner surface 12*ia*, a second inner surface 12*ib* and a third inner surface 12*ic*. The first inner surface 12*ia* is a surface facing an outer circumferential face on which a bending wire 11 extends out toward the manipulator 5 across the gap 12*c* and set to have a friction coefficient $\mu 1$. The second inner surface 12*ib* is provided adjacent to the first inner surface 12*ia* and a friction coefficient $\mu 2$ thereof is set to be lower than the friction coefficient $\mu 1$. The third inner surface 12*ic* is provided adjacent to the second inner surface 12ib and a friction coefficient μ3 thereof is set to be lower than the friction coefficient μ2.

Note that a frictional resistance of the entire inner surface 12i may also be set so as to continuously increase in the circumferential direction from the first inner surface 12ic.

Figure 10:
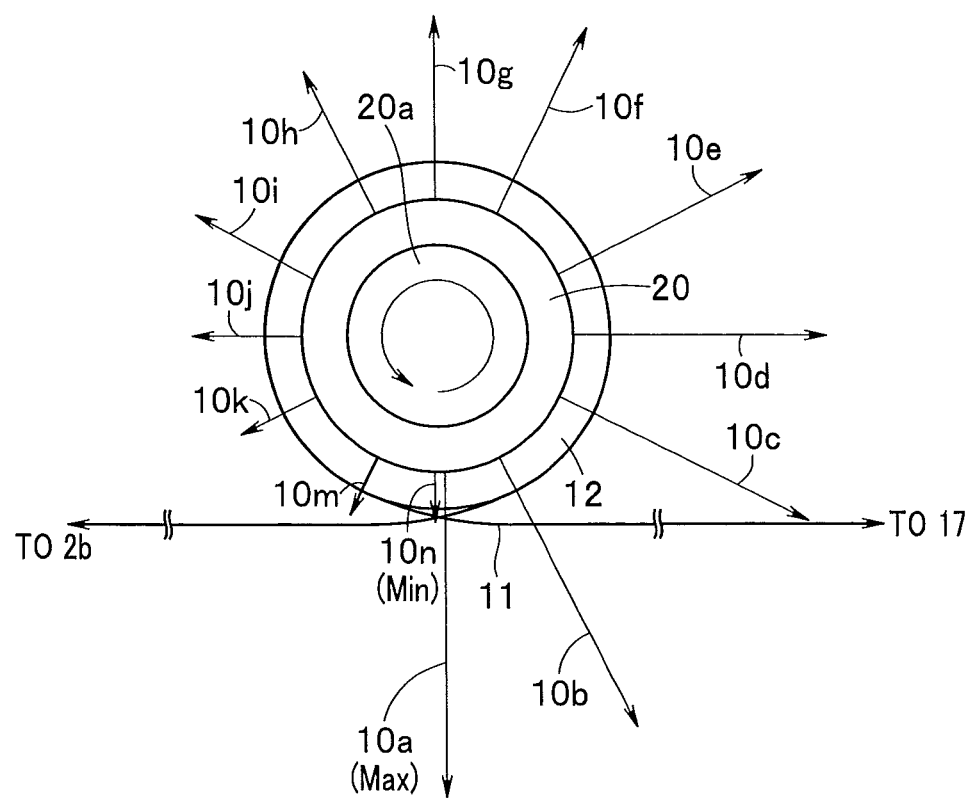

It is known that a magnitude of a normal force received by a rotating body 12 when an entire inner surface of the rotating body 12 is brought into close contact with the outer circumferential face of the pulley 20 is proportional to a length of a part of the bending wire 11 that is in close contact with the rotating body 12 and the normal force varies from a maximum normal force, which is indicated by arrow 10a in FIG. 10 to a minimum normal force indicated by arrow 10n in FIG. 10 along a logarithmic curve. Reference numeral 19 denotes a guiding roller, which is arranged between the guide roller 15r and the pulley 20.

As illustrated in FIG. 9A, an operation to tilt the manipulator 5 in, for example, the Yd direction is performed to pull a part on the manipulator 5 side of the bending wire 11, thereby narrowing the gap 12c of the rotating body 12. Then, the inner surface 12i of the rotating body 12A is pressed against the outer circumferential face of the pulley 20, whereby a normal force is generated. In this case, the rotating body 12A is moved so that the friction force is largest at a position where a maximum normal force is generated. In other words, the rotating body 12 is moved so that a region of the inner surface 12i having a large friction coefficient μ comes into contact with a part with a large normal force. Then, along with the movement of the rotating body 12, the part on the insertion portion 2 side of the bending wire 11 is pulled, whereby the bending portion 2b bends.

In the rotating body 12A in the present embodiment, as described above, a setting is made so that the friction coefficient of the inner surface 12i varies in a stepwise manner to the friction coefficients μ1, μ2 and μ3 along the circumferential direction within the predetermined range. Thus, when the operator performs an operation to further tilt the manipulator 5, the rotating body 12A is rotated to move the position of the inner surface 12i in the order of the third inner surface 12ic, the second inner surface 12ib and the first inner surface 12ia so that a friction force at the position where a maximum normal force is generated is a maximum friction force. Then, the bending portion 2b is gradually bent large.

As described above, in the present embodiment, with the bending of the bending portion 2b, an inner face of the inner surface 12i that has a high friction coefficient is moved to a position where a maximum normal force is generated. As a result, an assist for a force amount required for a bending operation is increased along with the bending angle increase, whereby the part of the bending wire 11 arranged on the insertion portion side is smoothly pulled and moved, enabling reduction in burden on the operator.

Note that, in the above-described embodiment, the setting for the initial rotation speed of the motor is changed to, for example, 1.1 times, 1.2 times, 0.9 times or 0.8 times relative to the rotation speed in the initial state to respond to demands by operators, that is, demands for operation with a little larger amount of strength or a little smaller amount of strength.

However, employment of the configuration indicated below enables responding to these demands by operators.

An endoscope including a pulling member operation apparatus according to a second embodiment of the present invention will be described with reference to FIGS. 11 to 16.

Figure 11:
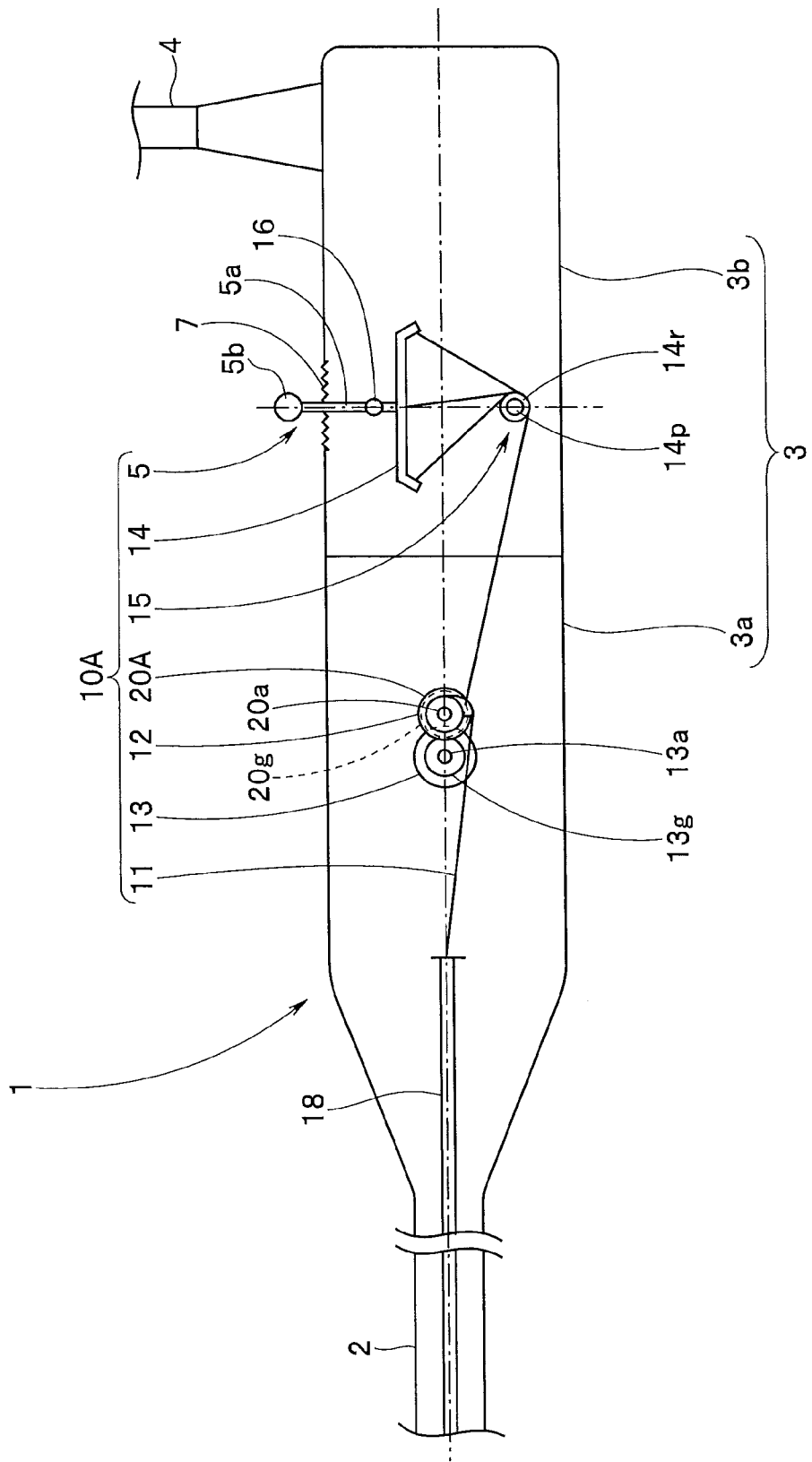
FIGS. 11 to 16 are diagrams relating to a second embodiment of the present invention.

As illustrated in FIG. 11, an endoscope 1 according to the present embodiment includes a pulling member operation apparatus 10A including a pulley 20A that doubles as a force amount adjustment section inside an operation portion 3. The rest of the configuration of the pulling member operation apparatus 10A is similar to that of the first embodiment, and members that are the same as those of the first embodiment are provided with reference numerals that are the same as those of the first embodiment and a description thereof will be omitted.

A configuration of the pulley 20A will be described with reference to FIGS. 12 to 15.

Figure 12:
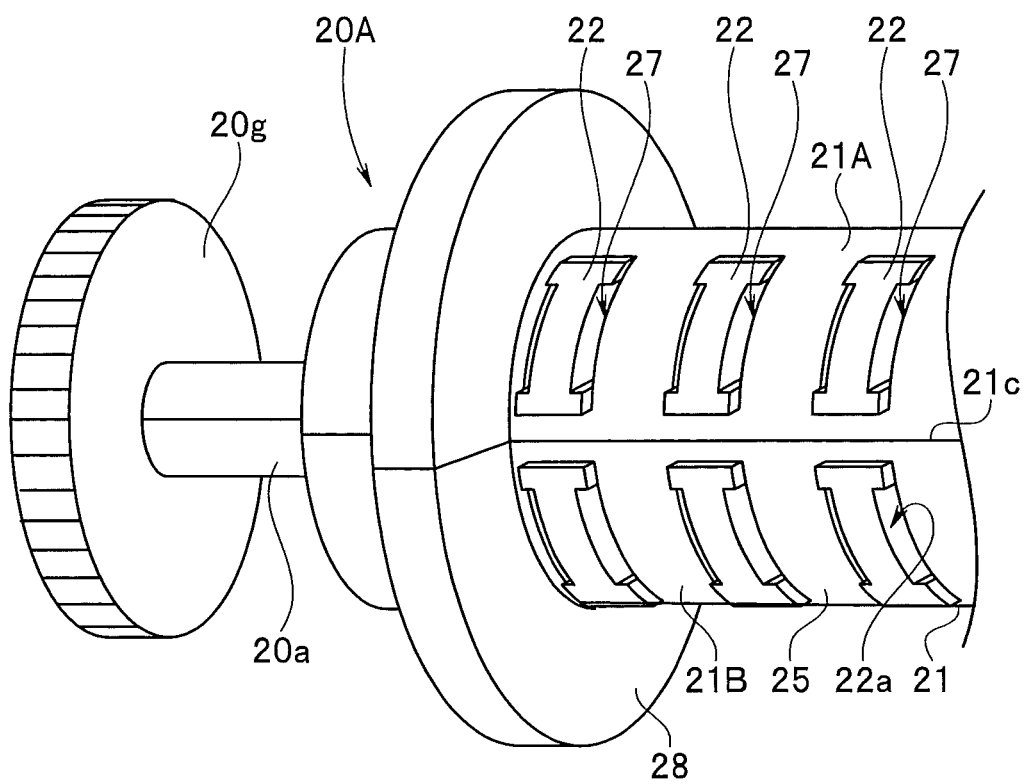
Figure 13:
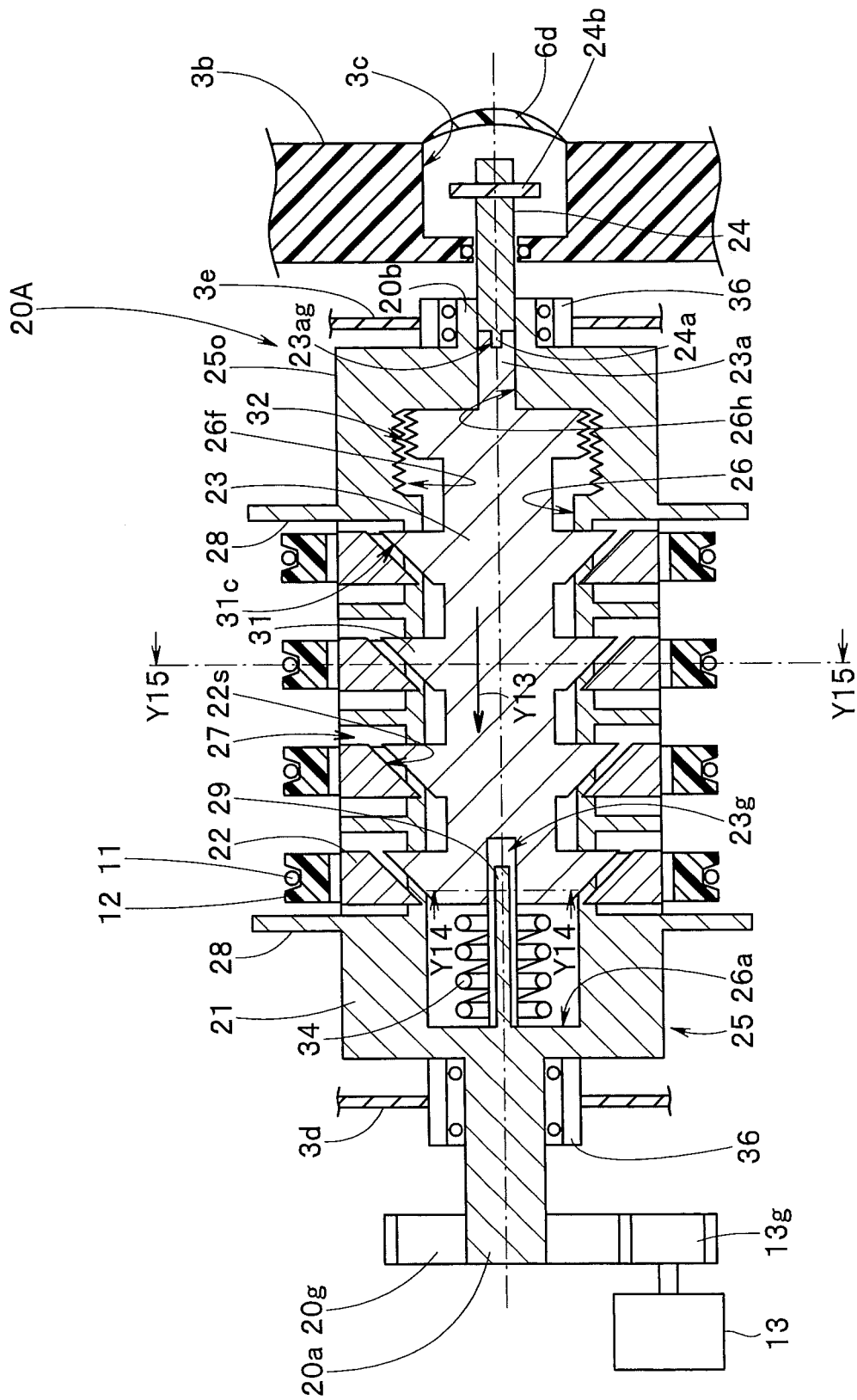

As illustrated in FIGS. 12 and 13, the pulley 20A mainly includes a pulley body 21, moving pulley pieces 22, a pulley piece position adjustment bar (hereinafter abbreviated as adjustment bar) 23 and an adjustment shaft 24.

The pulley body 21 is a first pulley portion and mainly includes a barrel portion 25, an adjustment bar disposition space 26, moving pulley piece disposition holes (hereinafter abbreviated as moving holes) 27, a pair of flange portions 28, a pulley shaft 20a and a support shaft 20b. A pulley-side gear 20g is fixed to the pulley shaft 20a.

In the present embodiment, as illustrated in FIG. 12, the pulley body 21 is divided in two parts, i.e., a first pulley body 21A and a second pulley body 21B. The first pulley body 21A and the second pulley body 21B are a pair of semicircular column bodies each having a semicircular shape in cross-section, and reference numeral 21c denotes a parting line.

The first pulley body 21A and the second pulley body 21B are integrally fixed to each other via, for example, screws or bonding. Upon the first pulley body 21A and the second pulley body 21B being integrally fixed to each other, the pulley body 21 including the barrel portion 25 having a circular shape in cross section, the pulley shaft 20a, the support shaft 20b and the flange portions 28 is provided.

In the present embodiment, the first pulley body 21A and the second pulley body 21B are integrally fixed to each other via screws. Thus, for example, female threads (not illustrated) are formed in the first pulley body 21A, and holes for arranging male-thread screws that threadably engage with the female threads, i.e., what are called counterbores (not illustrated) are formed in the second pulley body 21B.

As illustrated in FIG. 13, the adjustment bar disposition space 26 is an axial space formed in an elongated shape in an axis direction, which is formed in the barrel portion 25. The adjustment bar disposition space 26 is an inner space in which the adjustment bar 23 is slidably arranged. The adjustment bar disposition space 26 is provided by combining semicircular recess portions each having a semicircular shape in cross section formed on the respective flat face sides of the first pulley body 21A and the second pulley body 21B facing each other. In the vicinity of an end face on the support shaft 20b side of the adjustment bar disposition space 26, a female thread portion 26f included in a sliding mechanism portion is provided. Reference numeral 26h denotes a side hole, which is a round hole that makes the adjustment bar disposition space 26 and an outer portion on the end face side of the support shaft 20b in communication with each other.

The moving holes 27 are communications holes that make the inner faces of the semicircular recess portions and an outer face of the barrel portion 25 in communication with each other and each have a substantially rectangular shape. The moving holes 27 are arranged in the first pulley body 21A and the second pulley body 21B in such a manner that, for example, four are arranged in one row at predetermined intervals and two such rows are arranged.

The flange portions 28 project from respective outer circumferential faces on the respective end face sides by a predetermined amount. In the barrel portion 25 between the pair of flange portions 28, four moving holes 27 are arranged circumferentially at equal intervals and four moving holes are arranged longitudinally at equal intervals.

Figure 14:
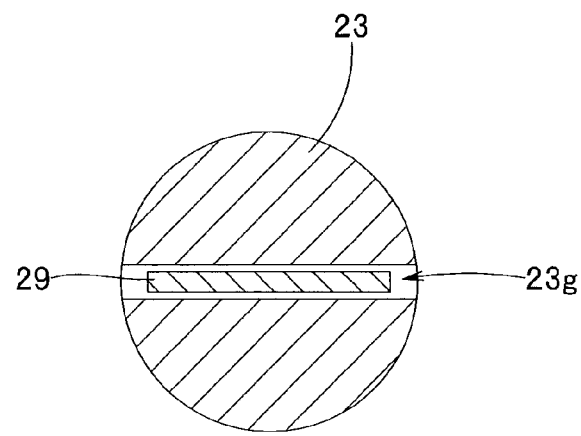
Figure 15:
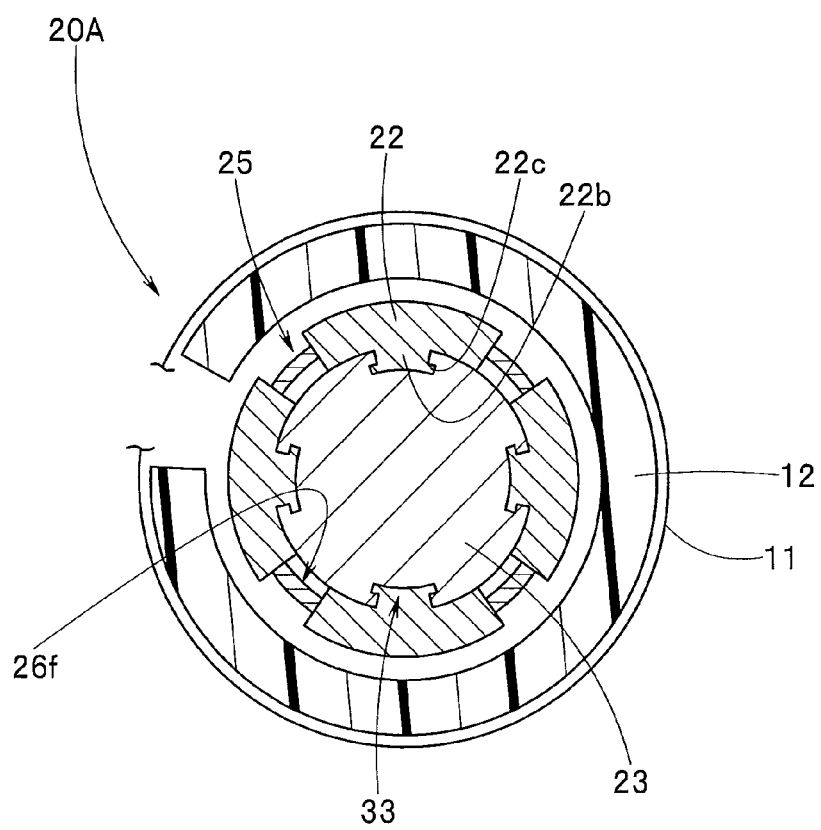

Reference numeral 29 denotes an engaging insertion projection. The engaging insertion projection 29 projects from an inner end face 26a on the pulley shaft 20a side of the adjustment bar disposition space 26 by a predetermined amount. The engaging insertion projection 29 is arranged inside an engaging insertion groove 23 formed in the adjustment bar 23, which will be described later. As illustrated in FIG. 14, a cross-sectional shape of the engaging insertion projection 29 is, for example, a rectangular shape. The engaging insertion projection 29 serves as both of a joining portion for rotating the pulley body 21 and the adjustment bar 23 in an integrated manner and a defining portion for disposing the adjustment bar 23 with a predetermined orientation inside the adjustment bar disposition space 26.

The moving pulley pieces 22, which provide a second pulley portion, are slidably arranged inside the respective moving holes 27. The moving pulley pieces 22 can move from the center axis side of the adjustment bar disposition space 26 toward the outside inside the moving holes 27 and can also move in a direction opposite to such direction. End faces on the adjustment bar disposition space center axis side of the moving pulley pieces 22 arranged in the moving holes 27 are slant surfaces 22s formed so as to have a predetermined orientation and a predetermined inclination angle. A cam surface 31c of a cam portion 31, which will be described later, is arranged so as to abut each of the slant surfaces 22s.

In the present embodiment, ridge lines of each of the moving pulley pieces 22 are chamfered to have a curved surface shape. The chamfered moving pulley pieces 22 smoothly slide relative to the moving holes 27. Reference numeral 22a in FIG. 12 denotes a clearance portion, which reduces a contact resistance between a moving pulley piece 22 and a moving hole 27.

The adjustment bar 23, which is included in the force amount adjustment section, includes a plurality of projection portions projecting toward the outer circumference. The adjustment bar 23 is a round bar and includes the engaging insertion groove 23g on the one end face side, and an engaging insertion shaft 23a is provided so as to project from the other end face side. A depth dimension of the engaging insertion groove 23g is set taking an amount of projection of the engaging insertion projection 29 into account, and a predetermined gap is formed between an end face of the engaging insertion projection 29 and a bottom face of the engaging insertion groove 23g. The gap is set to be larger than an amount of movement of the adjustment bar 23, which will be described later. The engaging insertion shaft 23a is arranged inside the side hole 26h by means of fitting in a predetermined manner. In an end face of the engaging insertion shaft 23a, a positioning groove 23ag is formed. A projection 24a of the adjustment shaft 24 is arranged in the positioning groove 23ag and the projection 24a and the positioning groove 23ag are integrally fixed to each other by means of, e.g., bonding.

The plurality of projection portions of the adjustment bar 23 include a plurality of cam portions 31 and a moving thread portion 32. The moving thread portion 32, which is included in a slide mechanism portion, is provided on the engaging insertion projection 29 side. The moving thread portion 32 is arranged so as to be threadably connected to the female thread portion 26f.

Among the cam portions 31, four are provided in a circumferential direction of an outer circumferential face of the adjustment bar 23 at equal intervals and four are provided in a longitudinal direction of the barrel portion 25 at equal intervals. The cam portions 31 each include a cam surface 31c, which is an inclined surface that abuts the slant surface 22s of the respective moving pulley pieces 22. In the initial state illustrated in FIG. 13, the cam surfaces 31c are provided so as to face the respective slant surfaces 22s with a small space therebetween.

In each cam surface 31c, a coming-off prevention portion (see reference numeral 33 in FIG. 15) is formed. The coming-off prevention portion 33 is a groove that prevents the corresponding moving pulley piece 22 from coming off from the corresponding moving hole 27 toward the outside of the barrel portion 25. In the coming-off prevention portion 33, an engaging insertion portion 22c provided at a corresponding projection 22b is arranged. The projection 22b is configured so as to project from the relevant moving pulley piece 22 toward the adjustment bar disposition space center axis side.

With such configuration, as indicated by arrow Y13 in FIG. 13, the adjustment bar 23 is moved toward the motor 13 side along a longitudinal axis, whereby the cam surfaces 31c come into contact with the slant surfaces 22s. Subsequently, the cam surfaces 31c are further moved in the same direction, whereby the moving pulley pieces 22 are moved from the center axis side of the adjustment bar disposition space 26 toward the outside inside the respective moving holes 27. In other words, the moving pulley pieces 22 come out from respective openings on the barrel portion 25 side of the moving holes 27 and approach inner surfaces of corresponding rotating bodies 12.

Note that in FIG. 13, reference numeral 3c denotes an adjustment hole, which is formed in a side face of the operation portion body 3b. The adjustment hole 3c is occluded by a cap body 6d. The cap body 6d is an elastic body that is removable from the adjustment hole 3c, and protects the inside of the adjustment hole 3c in a watertight manner. Inside the adjustment hole 3c, an end portion of the adjustment shaft 24 is arranged. Opposite end portions of a stick-like protrusion 24b project from an outer circumferential face of the end portion of the adjustment shaft 24, respectively.

Figure 16:
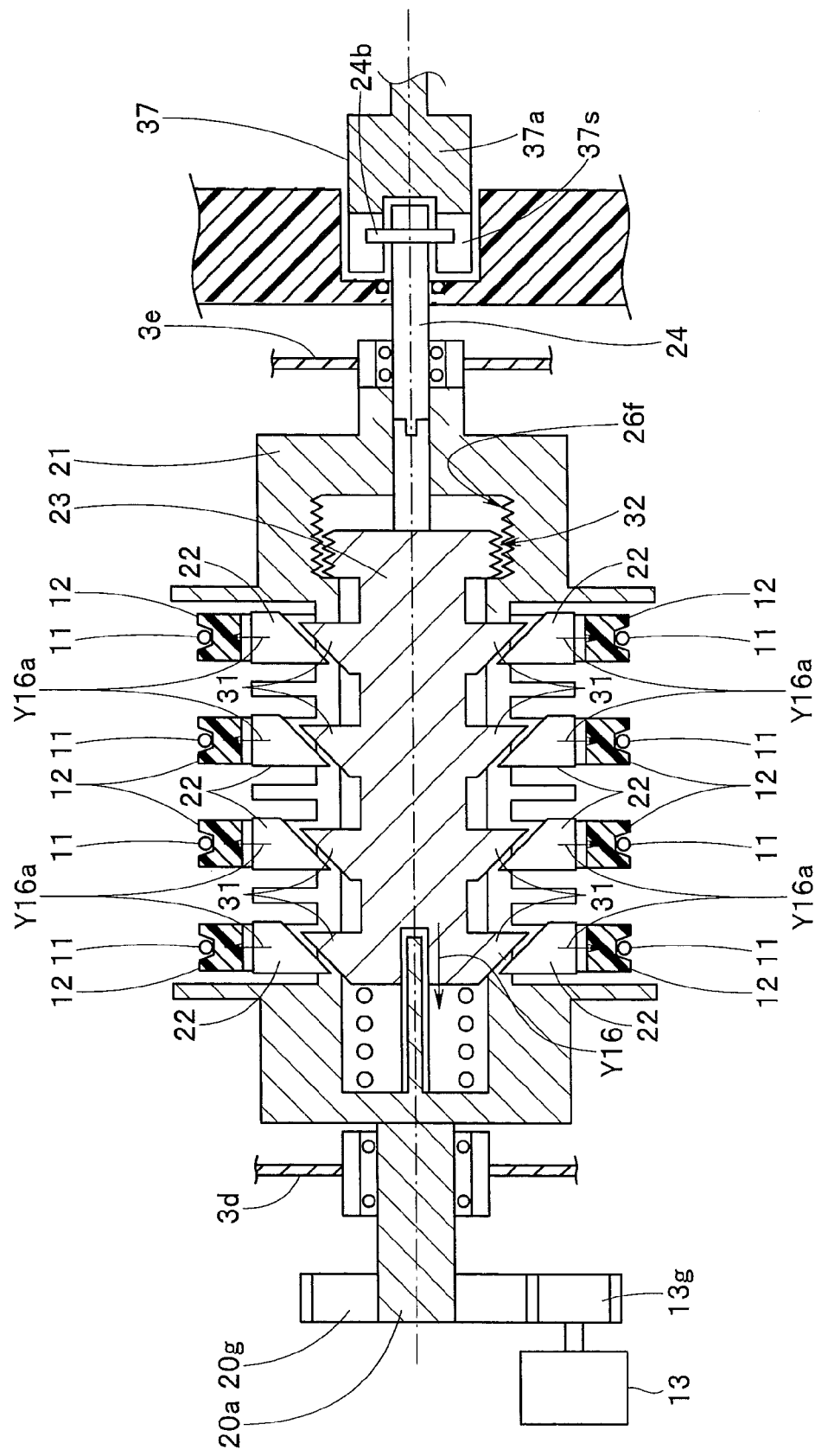

The stick-like protrusion 24b is configured so as to be engaged in a slit 37s formed at an end portion of a rotating tool (see reference numeral 37 in FIG. 16). A distance from a bottom face of the adjustment hole 3c to an end face of the stick-like protrusion 24b is set to be larger than an amount of movement of the adjustment bar 23.

Also, reference numeral 34 denotes a spring. The spring 34 biases the adjustment bar 23 toward the adjustment hole 3c, which is a direction opposite to arrow Y13, by means of a predetermined biasing force.

Furthermore, reference numerals 3d and 3e denote frame bodies, which are provided inside the operation portion body 3b. In the first frame body 3d, a first support body arrangement hole is formed. In the first support body arrangement hole, a first support body 35 that pivotably supports the pulley shaft 20a of the pulley body 21 is arranged, and in the second frame body 3e, a second support body arrangement hole is formed. In the second support arrangement hole, a second support body 36 that pivotably supports a support shaft 20b of the pulley body 21 is arranged.

Here, an operation of the endoscope 1 including the pulling member operation apparatus 10A inside the operation portion 3, the pulling member operation apparatus 10A including the pulley 20A that doubles as the force amount adjustment section, will be described.

When an operator operates the endoscope 1, the operator adjusts an amount of projection of the moving pulley pieces 22 from the respective openings on the barrel portion 25 side of the respective moving holes 27 so that an operation to tilt a manipulator 5 can be performed with a desired manipulator tilting operation force amount.

In such case, the operator prepares the rotating tool 37. As illustrated in FIG. 16, the operator removes the cap body 6d to expose the stick-like protrusion 24b inside the adjustment hole 3c. Then, the operator arranges a distal end portion 37a of the rotating tool 37 inside the adjustment hole 3c to guide the stick-like protrusion 24b into the slit 37s formed in the distal end portion 37a.

Next, the operator rotates a non-illustrated handle of the rotating tool 37 clockwise. Then, the adjustment shaft 24 rotates and the rotation is transmitted to the engaging insertion shaft 23a, and the moving thread portion 32 arranged so as to threadably connected to the female thread portion 26f starts moving while rotating. Then, the adjustment bar 23 gradually moves toward the motor 13, which is the arrow Y16 direction, against the biasing force of the spring 34. Also, along with the movement of the adjustment bar 23, the cam surfaces 31c also move in the same direction and thereby come into contact with the respective slant surfaces 22s.

Here, the operator continues to rotate the rotating tool 37 clockwise. Then, the adjustment bar 23 further moves in the arrow Y16 direction, whereby the cam surfaces 31c also move in the same direction. Along with the movement of the cam surfaces 31c, all the moving pulley pieces 22 gradually project in the arrow Y16a direction, that is, from the barrel portion 25-side openings of the respective moving holes 27.

Here, the operator arbitrarily brings the motor 13 into a driving state to rotate the pulley 20A, and checks an operational feeling while performing an operation to tilt the manipulator 5. Then, adjustment is made by repeating movement of the adjustment bar 23 using the rotating tool 37 and a tilting operation of the manipulator 5 so as to obtain an optimum operational feeling.

Note that if the handle of the rotating tool 37 is rotated counterclockwise, the adjustment bar 23 gradually moves in a direction opposite to the arrow Y16 direction by means of the biasing force of the spring 34.

In the present embodiment, in the state illustrated in FIG. 13, that is, when the engaging insertion groove-side of the adjustment bar 23 including the engaging insertion shaft 23a is farthest from the motor 13, outer circumferential faces of the moving pulley pieces 22 are closest to an axis center of the pulley body 21.

Then, as illustrated in FIG. 16, when the adjustment bar 23 is moved furthest to the arrow Y16 direction, the outer circumferential faces of the moving pulley pieces 22 are farthest from the axis center of the pulley body 21. At this time, a distance from the axis center of the pulley body 21 to a friction force generation site is longest, and thus, a largest torque, in other words, a largest assist force amount can be obtained. Here, a friction force generation site is a surface of contact between the outer circumferential face of a moving pulley piece 22 and the inner surface of a rotating body 12.

After completion of adjustment of the position of the adjustment bar 23, the operator starts an examination using the endoscope 1. At this time, as described in the above-described first embodiment, when a shaft portion 5a of a manipulator 5 is in a standing state upon the motor 13 being driven to rotate the pulley 20A, the bending portion 2b is held in a linear state. At this time, as illustrated above, the respective bending wires 11 wound on the respective four rotating bodies 12, which are arranged on pulley 20A and respectively correspond to the upper, lower, left and right directions, are all in a predetermined loosened state. As a result, all the rotating bodies 12 slide relative to the pulley 20.

On the other hand, when the operator performs an operation to tilt the shaft portion 5a of the manipulator 5 with grasping a grasping portion 3a in order to perform an operation to bend the bending portion 2b, for example, upward, along with the tilting operation, the suspension frame 14 inclines. As a result, the loosened state of the upward bending wire 11 gradually changes to a pulled state. On the other hand, the other bending wires 11 change to a further loosened state.

As a result, as in the first embodiment, from among the bending wires 11 wound on the four rotating bodies 12 on the pulley 20A, only the upward bending wire 11 is pulled. Then, a gap 12c in the rotating body 12 for upward bending is narrowed against an elastic force, whereby the inner surface of the rotating body 12 for upward bending changes to a diameter-reduced state in which the inner surface is in close contact with the outer circumferential face of the corresponding moving pulley piece 22.

As a result, a frictional resistance is generated between the rotating body 12 for upward bending and the corresponding moving pulley piece 22, whereby the rotating body 12 for upward bending is rotated in a direction that is the same as a direction of rotation of the pulley 20A. Along with the rotation of the rotating body 12 for upward bending, a part of the upward bending wire 11 arranged on the insertion portion 2 side relative to the rotating body 12 for upward bending is pulled and thereby moved, whereby the bending portion 2b starts operation to bend upward.

The operator performs the operation to tilt the shaft portion 5a in the same direction continuously from the start of the operation to bring the inner surface of the rotating body 12 for upward bending into close contact with the outer circumferential face of the moving pulley piece 22. As a result, the part of the upward bending wire 11 positioned on the insertion portion 2 side relative to the rotating body 12 for upward bending is further pulled and moved, whereby the bending portion 2b further bends upward. At this time, the operator can perform the tilting operation of the manipulator 5 with a predetermined optimum operational feeling.

As described above, the rotating tool 37 is arranged in the adjustment hole 3c provided in the operation portion 3 to rotate the adjustment shaft 24, whereby the adjustment bar 23 included in the pulley 20A in the pulling member operation apparatus 10A moves so as to advance/retract in an axis direction of the pulley body 21. As a result, the distance from the axis center of the pulley body 21 to the outer circumferential faces of the moving pulley pieces 22 can arbitrarily be set in a non-step manner to adjust an assist force amount.

Accordingly, even if there are differences among operators, such as whether the operators have large or small strength or the operators have large hands or small hands, the operators perform adjustment work for themselves, enabling a tilting operation to be performed with an optimum operational feeling for the respective operators.

Note that, in the above-described pulley 20A, the outer circumferential faces of the moving pulley pieces 22 are brought into contact with the inner surfaces of the rotating bodies 12 to adjust the distance from the axis center of the pulley body 21 to the outer circumferential faces of the moving pulley pieces 22.

Figure 17:
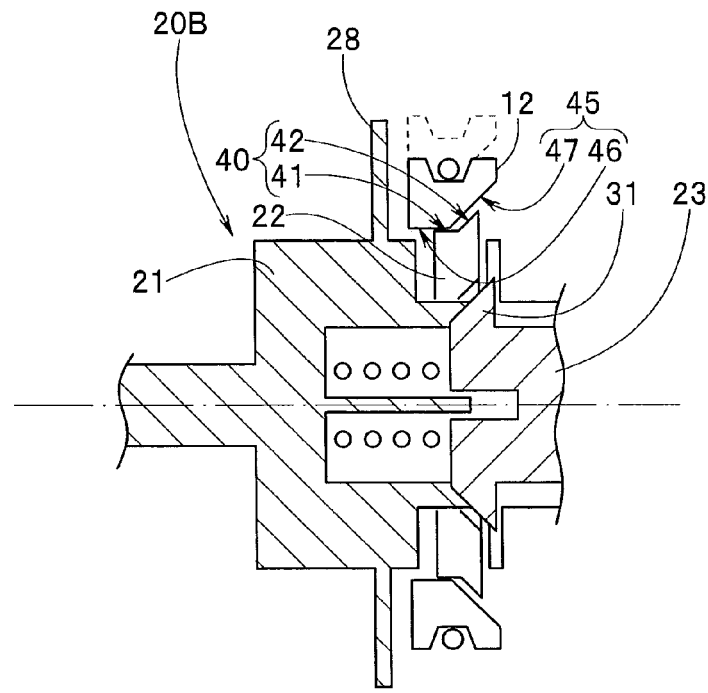
FIG. 17 is a diagram illustrating another configuration of a moving pulley piece.

In a pulley 20B, which is illustrated in FIG. 17, a configuration in which an outer circumferential face 40 of each moving pulley piece 22 includes a pulley-side straight surface 41 and a pulley-side inclined surface 42. Also, at the inner surface 45 side of each rotating body 12, a rotating body straight surface 46 and a rotating body inclined surface 47 are provided. The rotating body straight surfaces 46 are in surface-contact with the pulley-side straight surfaces 41, and the rotating body inclined surfaces 47 are in surface-contact with the pulley-side inclined surfaces 42.

As a result, the area of the outer circumferential face 40 including the pulley-side inclined surface 42 of each moving pulley piece 22 increases relative to the area of the outer circumferential face of each moving pulley piece 22 in the second embodiment. Thus, when the outer circumferential face of a moving pulley piece 22 is brought into contact with the inner surface 45 of the corresponding rotating body 12, the area of the contact increases, enabling provision of a larger assist force amount.

The rest of operation and effects are similar to those of the above-described second embodiment.

Also, in the above-described pulley 20A, an assist force amount can be adjusted by moving the adjustment bar 23 to advance/retract in the axial direction of the pulley body 21 to set a distance from the axis center of the pulley body 21 to the outer circumferential faces of the moving pulley pieces 22 in a non-step manner.

Figure 18:
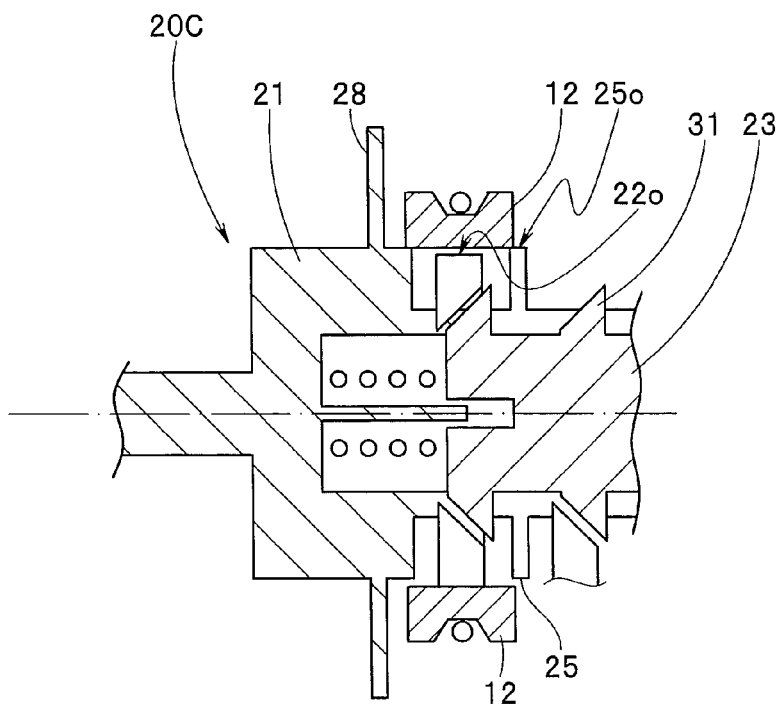
FIG. 18 is a diagram illustrating another configuration of a pulley included in a pulling member operation apparatus, in which an assist force amount is switched between two levels.

However, it is also possible to switch an assist force amount between two levels by moving the adjustment bar 23 to advance/retract in the axis direction of the pulley body 21 as with a pulley 20C, which is illustrated in FIG. 18.

In the pulley 20C, in an initial state, as illustrated in the diagram of the side above the center line of FIG. 18, an inner surface of each rotating body 12 is in contact with an outer circumferential face 25o of a barrel portion 25 of a pulley body 21. In other hand, when an adjustment bar 23 is moved to the motor side of the pulley body 21, as illustrated in the diagram on the lower side relative to the center line of FIG. 18, an outer circumferential face 22o of each moving pulley piece 22 is brought into contact with the inner surface of the corresponding rotating body 12.

Then, in the present embodiment, where a first friction coefficient of the outer circumferential face 25o of the barrel portion 25 is μ1 and a second friction coefficient of the outer circumferential face 22o of each moving pulley piece 22 is μ2, the following relationship is set between the first friction coefficient μ1 and the second friction coefficient μ2:

$$\mu 2 > \mu 1.$$

As a result, arbitrary setting of the friction coefficients μ1 and μ2 reduces an amount of movement of the adjustment bar 23 relative to the pulley body 21, enabling provision of two predetermined different assist force amounts.

The rest of operation and effects are similar to those of the above-described second embodiment.

Note that, in the pulley 20C in FIG. 18, the friction coefficients of the outer circumferential face 25o of the barrel portion 25 and the outer circumferential faces 22o of the moving pulley pieces 22 are arbitrarily set to provide two different assist force amounts.

Figure 19A:
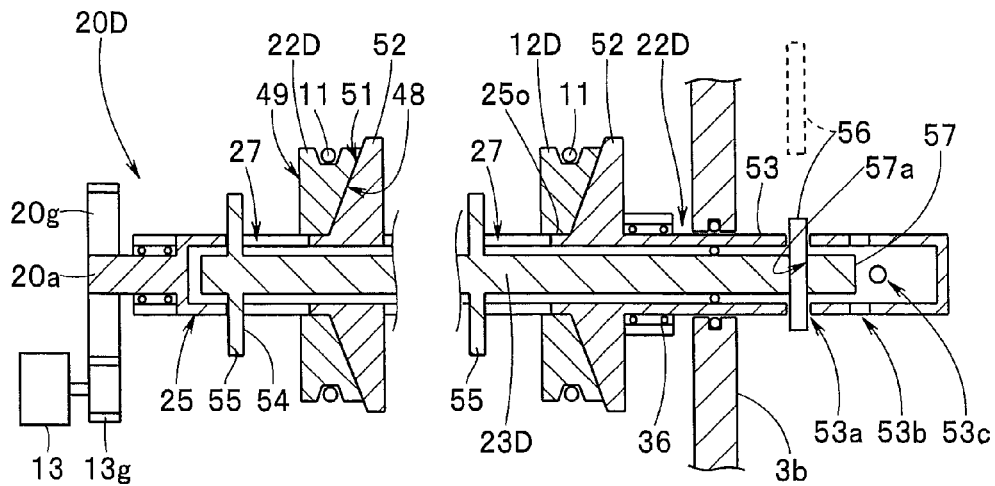
FIGS. 19A to 19C relate to another configuration of a pulley included in a pulling member operation apparatus.

On the other hand, as illustrated in FIG. 19A, a pulley 20D according to the present embodiment has a configuration in which the assist force amount can be switched among three levels by moving a position of an adjustment bar 23D in an axis direction. Thus, instead of the female thread portion 26f and the moving thread portion 32, the pulley 20D includes positioning holes 53a, 53b and 53c, a fixing pin 56 and a through hole 57a, which will be described later.

A configuration and operation of the pulley 20D will be described with reference to FIGS. 19A and 19B.

The pulley 20D according to the present embodiment mainly includes a pulley body 21D, moving pulley pieces 22D and an adjustment bar 23D. In the Figures, from among four moving pulley pieces 22D, a part of a pulley body 21D and a part of an adjustment bar 23D for two moving pulley pieces 22D will be illustrated and illustration of the others is omitted.

Each moving pulley piece 22D doubles as a rotating body 12 and includes a slant surface 48 and an abutment surface 49. The rest of the configuration is similar to that of the second embodiment, and members that are the same as those of the second embodiment are provided with reference numerals that are the same as those of the second embodiment and a description thereof will be omitted.

The pulley body 21D includes four projection portions 52 each including an inclined surface 51 on which a slant surface 48 is arranged so as to abut thereto. The projection portions 52 project from outer circumferential faces 25o of a barrel portion 25. Also, the pulley body 21D includes a projection arrangement portion 53 that doubles as a first support shaft projecting from the operation portion body 3b. At predetermined positions in the projection arrangement portion 53, three positioning holes 53a, 53b and 53c are formed. In the respective positioning holes 53a, 53b and 53c, a round stick-like fixing pin 56 is inserted. An axis of the first positioning hole 53a and an axis of the second positioning hole 53b are parallel to each other. The axis of the first positioning hole 53a and an axis of the third positioning hole 53c are orthogonal to each other and the axis of the second positioning hole 53b and the axis of the third positioning hole 53c are orthogonal to each other. The rest of the configuration is similar to that of the second embodiment, and members that are the same as those of the second embodiment are provided with reference numerals that are the same as those of the second embodiment and a description thereof will be omitted.

The adjustment bar 23D includes four pressing portions 55 at predetermined intervals. Each pressing portion 55 is a projection portion including a pressing surface 54 that presses the corresponding abutment surface 49. At a predetermined position in an end portion 57 of the adjustment bar 23D, through holes 57a to which the fixing pint 56 is inserted are provided. The end portion 57 is arranged outside the operation portion. The rest of the configuration is substantially similar to that of the second embodiment, and members that are the same as those of the second embodiment are provided with reference numerals that are the same as those of the second embodiment and a description thereof will be omitted.

In the present embodiment, as illustrated in FIG. 19A, as a result of the fixing pin 56 being arranged in the first positioning hole 53a and the through hole 57a, the adjustment bar 23D is arranged at a first position. In such arrangement state, the moving pulley pieces 22D are arranged on the respective outer circumferential faces 25o of the barrel portion 25, and the slant surfaces 48 are arranged so as to abut the corresponding inclined surfaces 51 of the projection portions 52.

Figure 19B:
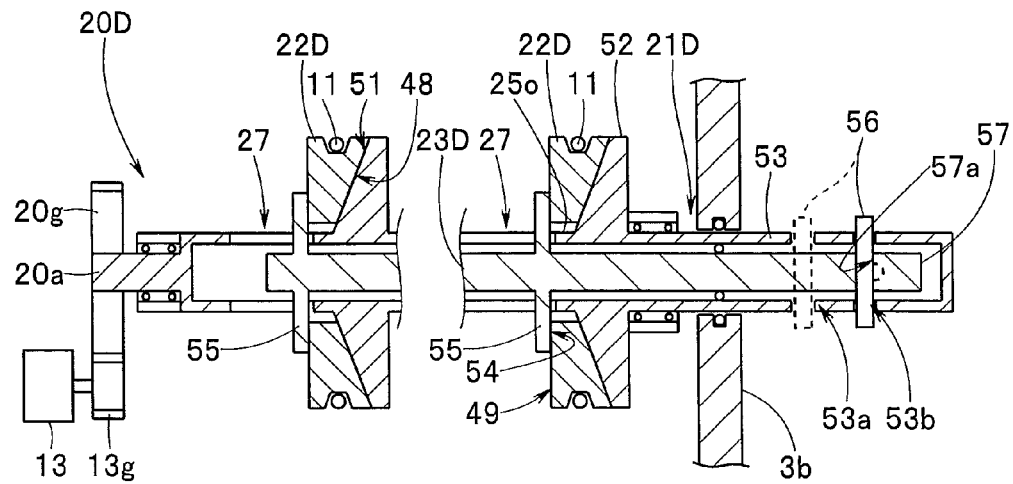

On the other hand, as illustrated in FIG. 19B, the position of the fixing pin 56 is switched to arrange the pin 56 in the second positioning hole 53b and the through hole 57a. As a result, the adjustment bar 23D is moved from the first position to a second position. As a result of the adjustment bar 23D being moved to the second position, the pressing surfaces 54 of the respective pressing portions 55 included in the adjustment bar 23D press the abutment surfaces 49 of the respective moving pulley pieces 22D. As a result, the slant surfaces 48 of the moving pulley pieces 22D move on inclined surfaces 51 of the projection portions 52 away from the respective outer circumferential faces 25o. In other words, the positions of the moving pulley pieces 22D move outward from the axis center of the pulley body 21D.

Figure 19C:
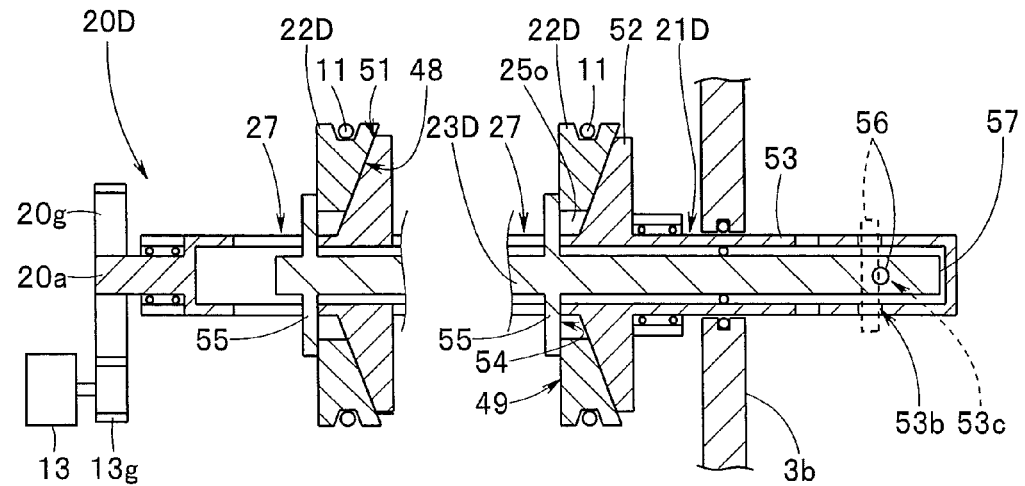

Furthermore, the position of the fixing pin is changed so as to arrange the fixing pin 56 to be engaged in the third positioning hole 53c and the through hole 57a as illustrated in FIG. 19C. As a result, the adjustment bar 23D is moved from the second position to a third position. As a result of the adjustment bar 23D being moved to the third position, the pressing surfaces 54 of the respective pressing portions 55 included in the adjustment bar 23D press the abutment surfaces 49 of the respective moving pulley pieces 22D to move the moving pulley pieces 22D further away from the outer circumferential faces 25o. Then, positions of the outer circumferential faces of the moving pulley pieces 22D are changed to farthest positions relative to the axis center of the pulley body 21D.

In this case, a distance from the axis center of the pulley body 21D to a friction force generation site becomes longest, resulting in a condition enabling provision of a largest assist force amount. Here, "friction force generation site" refers to a surface of contact between the inclined surface 51 of a projection portion 52 and the slant surface 48 of a moving pulley piece 22D.

As described above, the adjustment bar 23D is arranged so as to be fixed at any of the first position, the second position and the third position, which are different from one another in the axis direction, enabling three-level switching of the assist force amount.

A configuration and operation of a pulley 20E will be described with reference to FIGS. 20 to 22.

Figure 20:
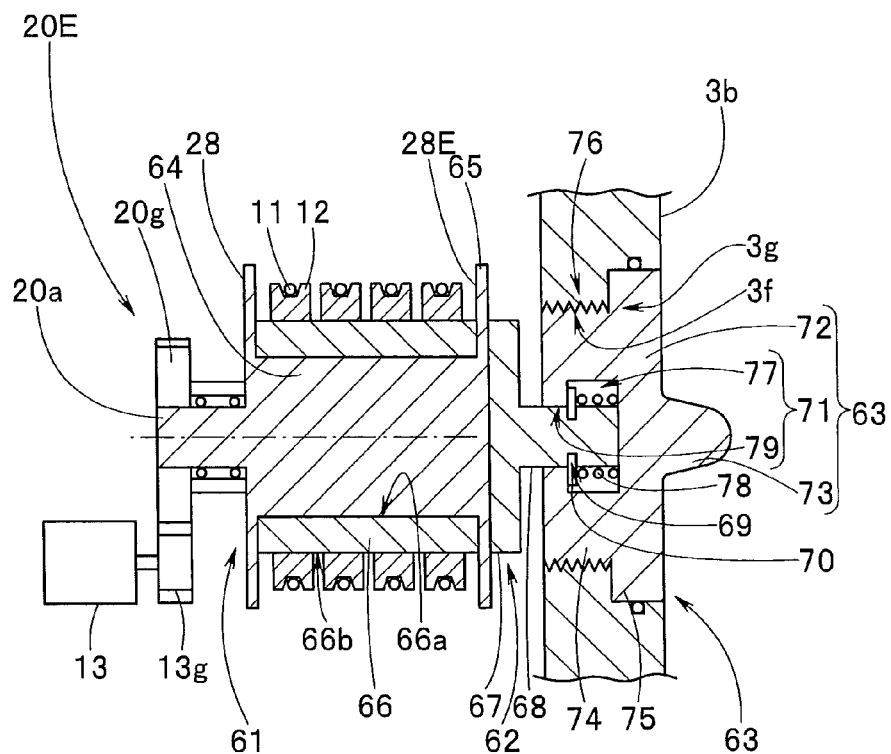
FIGS. 20 to 22 relate to still another configuration of a pulley whose assist force amount is changed in a stepwise manner.

As illustrated in FIG. 20, the pulley 20E according to the present embodiment mainly includes a first pulley portion 61, a plurality of second pulley portions 62 and an attachment 63. The first pulley portion 61 is disposed inside the operation portion 3. The plurality of second pulley portions 62 are replaceable ones and are attached to/removed from an operation portion body 3b of an operation portion 3 via the attachment 63.

The first pulley portion 61 includes a pulley shaft 20a, a barrel portion 64 and a pair of flange portions 28. On the barrel portion 64, a plurality of rotating bodies 12 are arranged with a predetermined distance between the respective rotating bodies 12. The pair of flange portions 28 prevent the rotating bodies 12 from coming off from the barrel portion 64.

In the present embodiment, one of the flange portions 28E includes a plurality of flange-shaped portions 65. In other words, the flange portion 28E includes non-illustrated cuts in which later-described contact resistance portions 66 are arranged, at equal intervals in a circumferential direction.

A second pulley portion 62 is attachable to/detachable from the first pulley portion 61, and for the second pulley portion 62, for example, three types of second pulley portions 62A, 62B and 62C are provided. The second pulley portions 62A, 62B and 62C each include a plurality of contact resistance portions 66, a circular plate portion 67 and an attachment portion 68. The contact resistance portions 66 are a plurality of projection portions provided in a standing manner from one side of the circular plate portion 67. The contact resistance portions 66 are provided away from each other at equal intervals, and are provided on outer circumferential faces of the barrel portion 64 through the respective cuts arranged in the circumferential direction of the flange portion 28E. Reference numeral 66a denotes an inner surface of each contact resistance portion 66. The inner surface 66a is arranged on the outer circumferential face of the barrel portion 64.

On the outer circumferential face 66b side of the plurality of contact resistance portions 66, inner surfaces of the rotating bodies 12 are arranged in a predetermined loose-fit state.

The outer circumferential faces 66b of the contact resistance portions 66 are set to have a predetermined friction coefficient.

On the other hand, the second pulley portions 62A, 62B and 62C are set to have friction coefficients that are different from one another depending on the respective pulley portions. More specifically, the friction coefficient of the outer circumferential face 66b of the type-A second pulley portion 62A is $\mu 1$, the friction coefficient of the outer circumferential face 66b of the type-B second pulley portion 62B is $\mu 2$, and the friction coefficient of the outer circumferential face 66b of the type-C second pulley portion 62C is $\mu 3$.

The following relationship is set among $\mu 1$, $\mu 2$ and $\mu 3$:

$\mu 3 > \mu 2 > \mu 1$.

It has been described above that three types, i.e., type-A to type-C, of second pulley portions 62A, 62B and 62C are provided. However, three or more types of second pulley portions may be provided or two second pulley portions may be provided.

The circular plate portion 67 is a circular plate-shaped support body and has a predetermined thick dimension and a predetermined stiffness.

The attachment portion 68 is a projection provided so as to project from a center portion on the other side of the circular plate portion 67, and includes, for example, a circumferential groove 69 in which an E-ring 70 is arranged.

The attachment 63 mainly includes a joining portion 71, an attachment body 72 and a knob 73.

The joining portion 71 is pivotably joined to the attachment portion 68 of the second pulley portion 62. The attachment body 72 includes a small-diameter portion 74 and a large-diameter portion 75. The small-diameter portion 74 is arranged in a stepped hole 3g including a female thread portion 3f, which is included in the operation portion 3. In the small-diameter portion 74, a male thread portion 76 that is threadably connected to the female thread portion 3f is formed. The knob 73 is a projection portion projecting from an end face of the large-diameter portion 75. The knob 73 is formed so as to have a predetermined shape taking the handleability for operators into account.

Figure 21:
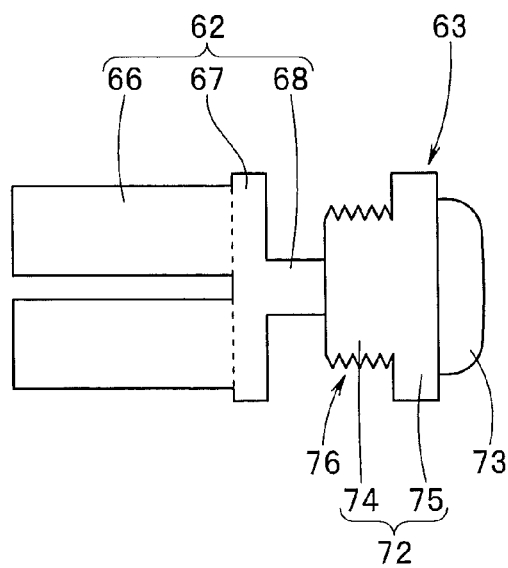
Figure 22:
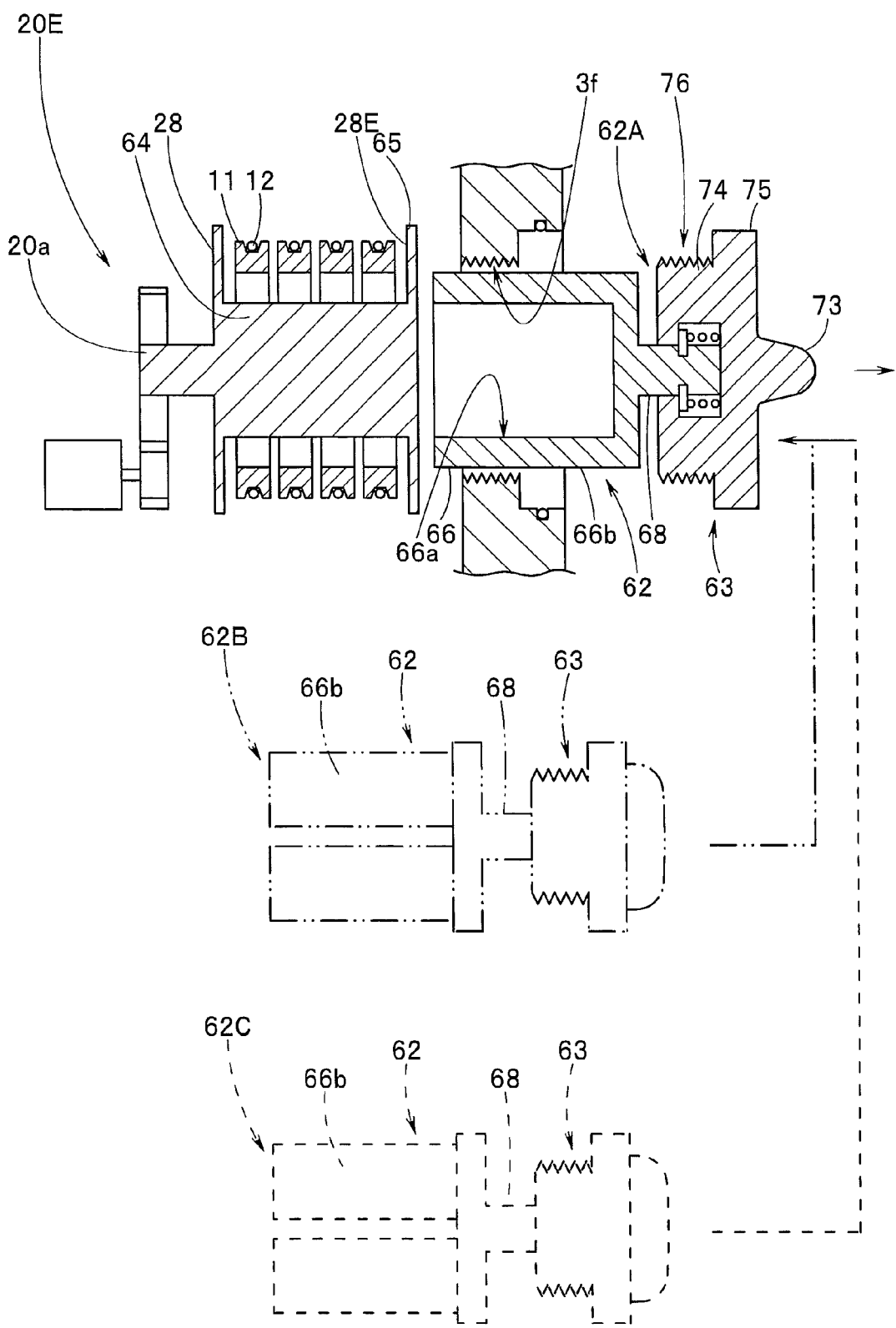

In the present embodiment, as illustrated in FIG. 21, the second pulley portion 62 and the attachment 63 are integrally formed in advance. In the present embodiment, for example, the small-diameter portion 74 and the large-diameter portion 75 included in the attachment 63 are separate bodies and integrally attached to each other by means of, e.g., bonding or screw shut. As illustrated in FIG. 20, in the small-diameter portion 74, a through hole 79 and a recess portion 77 included in the joining portion 71 are formed. The attachment portion 68 is inserted through the through hole 79. An E-ring 70 and a spring 78 are arranged in the recess portion 77.

The attachment portion 68 of the second pulley portion 62 is pivotably arranged in the small-diameter portion 74 so that the attachment portion 68 projects inside the recess portion 77 via the through hole 79 and the E-ring 70 is arranged so as to be engaged with the circumferential groove 69. In the attachment portion 68, the spring 78 having a predetermined biasing force and a predetermined length dimension is arranged. Then, the recess portion 77 is occluded by the large-diameter portion 75. In such case, the large-diameter portion 75 and the small-diameter portion 74 are integrally fixed to each other, via, for example, screws. Consequently, as illustrated in FIG. 21, the second pulley portion 62 and the attachment 63 are provided in an integrated manner.

In the present embodiment, the type-A second pulley portion 62A including the outer circumferential face 66b of the friction coefficient μ1, the type-B second pulley portion 62B including the outer circumferential face 66b of the friction coefficient μ2 and the type-C second pulley portion 62C including the outer circumferential face 66b of the friction coefficient μ3 are provided in advance. An operator selects an optimum one from among these second pulley portions 62A, 62B and 62C taking, e.g., the size of his/her hands or the grip strength into account.

As described above, in the present embodiment, an operator selects one from among a plurality of second pulley portions 62 with different friction coefficients for the first pulley portion 61, to provide the pulley 20E. As a result, a contact resistance between the outer circumferential face 66b of the second pulley portion 62A, 62B or 62C included in the pulley 20E and the inner surface of a rotating body 12 can be changed in a stepwise manner.

In the pulley 20E in which the second pulley portion 62 including the outer circumferential face 66b having a large friction coefficient is attached to the first pulley portion 61, a friction force between the inner surface of a rotating body 12 and the outer circumferential face 66b of the second pulley portion 62C is large, providing a larger assist force amount.

When an operator removes the second pulley portion 62A mounted in the operation portion 3, the operator grasps the knob 73 of the attachment 63 and rotates the knob 73, for example, counterclockwise. Then, the attachment body 72 is rotated relative to the operation portion body 3b and the attachment portion 68 and floats up from the operation portion body 3b. Then, the operator continues to operate the knob 73 to rotate the attachment body 72, whereby the attachment body 72 can be removed from the operation portion body 3b and the second pulley portion 62A can be removed from the first pulley portion 61.

Also, the operator mounts, for example, the second pulley portion 62C in the operation portion 3 instead of the second pulley portion 62A. In this case, contrary to the above procedure, first, the operator arranges the contact resistance portions 66 of the second pulley portion 62B on the first pulley portion 61 and also arranges the small-diameter portion 74 and the large-diameter portion 75 of the attachment body 72 in the stepped hole 3g in the operation portion body 3b.

The operator grasps the knob 73 of the attachment 63 and rotates the knob 73, for example, clockwise. Then, the attachment body 72 is rotated relative to the operation portion body 3b and the attachment portion 68, whereby the attachment body 72 is pressed into the stepped hole 3g and the contact resistance portions 66 move on the outer circumferential face of the barrel portion 64 of the first pulley portion 61 in the axis direction. Then, when an end face of the attachment body 72 and an outer surface of the operation portion body 3b are aligned with each other as a result of the operator continuing to operate the knob 73, attachment of the second pulley portion 62C to the first pulley portion 61 is completed.

Furthermore, although the above-described embodiment, a configuration in which a plurality of second pulley portions with different friction coefficients are provided is employed, a configuration in which a plurality of second pulley portions having different outer diameter dimensions are provided may be employed.

With such configuration, a second pulley portion having a largest outer diameter is mounted on a first pulley portion to provide a longest distance from a pulley shaft center to a friction force generation site, whereby a largest torque can be obtained and thus a larger assist force amount can be obtained. Here, "friction force generation site" refers to a contact surface between an outer circumferential face of the second pulley portion and an inner surface of a rotating body 12.

A configuration and operation of a pulley 20F will be described with reference to FIGS. 23 to 25.

Figure 23:
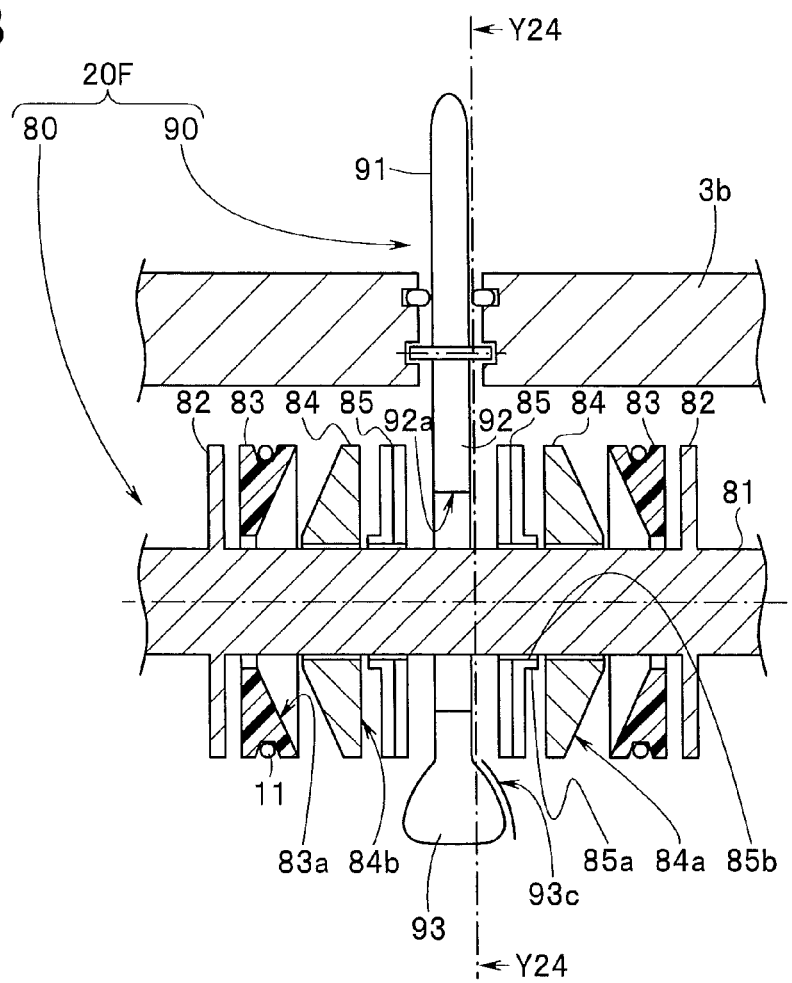
FIGS. 23 to 25 relate to another configuration in which a contact resistance between a pulley and rotating bodies is continuously changed.

As illustrated in FIG. 23, the pulley 20F according to the present embodiment mainly includes a pulley portion 80 disposed inside an operation portion 3, and an operation lever 90.

The pulley portion 80 according to the present embodiment includes a pulley shaft 81. The pulley shaft 81 includes a pair of flange portions 82, a pair of rotating bodies 83, a pair of contact resistance changing members 84 and a pair of pressing members 85.

As with the pulley shaft 20a, a pulley-side gear 20g is fixed to the pulley shaft 81. A motor-side gear 13g fixed to a motor shaft 13a of a motor 13 is engaged with the pulley-side gear 20g.

The pair of flange portions 82 are provided in a projecting manner at respective predetermined positions. Each of the pair of rotating bodies 83 has an elastically-deformable substantially circular plate shape and is disposed on the pulley shaft 81 in a predetermined loose-fit state.

Each of the pair of rotating bodies 83 includes a recess inclination side face 83a at a surface opposite to the flange portion 82 side. The recess inclination side faces 83a are inclined from an outer circumference toward a center. The rotating bodies 83 are slidably arranged on the pulley shaft 81.

Each of the pair of contact resistance changing members 84 includes a projecting inclination side face 84a. The projecting inclination side faces 84a are abutment surfaces to which the recess inclination side faces 83a of the rotating bodies 83 abut. The contact resistance changing members 84 each include a flat side face 84b including a flat surface. The flat side faces 84b are formed on the side opposite to the respective projecting inclination side faces 84a. The contact resistance changing members 84 are slidably arranged on the pulley shaft 81.

Each of a pair of pressing members 85 includes a pressing portion 85a and a bearing portion 85b. The pressing portions 85a press the flat side faces 84b of the contact resistance changing members 84. The bearing portions 85b are arranged on an outer circumferential face of the pulley shaft 81.

Figure 24:
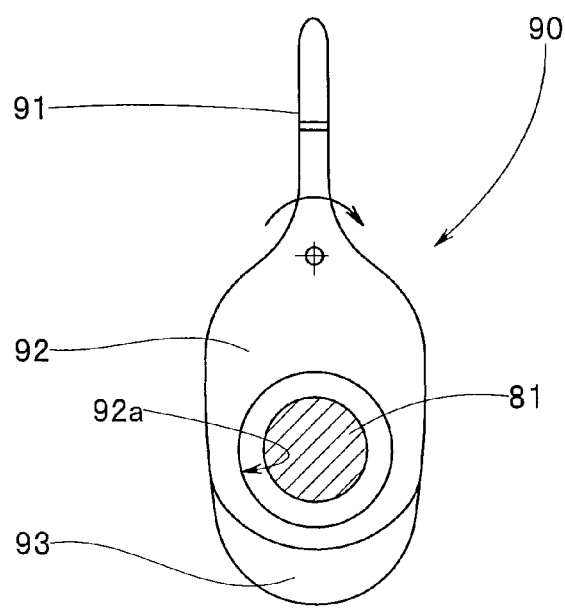

Also, as illustrated in FIGS. 23 and 24, the operation lever 90 is arranged orthogonal to the pulley shaft 81 of the pulley portion 80. The operation lever 90 includes a rod-like portion 91, a flattened portion 92 and a cam portion 93 in this order from the one end side. In the present embodiment, the rod-like portion 91 is provided so as to project outward from, for example, an upper face of the operation portion body 3b.

A through hole 92a through which the pulley shaft 81 is inserted is formed in the flattened portion 92. A diameter dimension of the through hole 92a is determined taking an amount of movement of the operation lever 90 into account. In other words, the through hole 92a has a gap of a size having a predetermined dimension relative to the pulley shaft 81.

In the cam portion 93, an inclined cam surface 93c is formed. The inclined cam surface 93c is inclined from a longitudinal center axis toward the outside of the other end. The inclined cam surface 93c abuts each of the pair of pressing members 85 as a result of the operation lever 90 being operated to bring the inclined cam surface 93c close to the pulley shaft center. After the abutment, the operation lever 90 is operated to bring the inclined cam surface 93c close to the pulley shaft center, and along with the operation, the pressing members 85 move on the pulley shaft 81 toward the respective flange portions 82.

Here, an operation of a pulling member operation apparatus including the pulley 20F will be described.

An operator brings a non-illustrated motor into a driving state to rotate the pulley 20F and performs a tilting operation of a manipulator 5. During the operation, if the operator has a heavy operational feeling, as described above, the operator operates the operation lever 90 to bring the inclined cam surface 93c close to the pulley shaft center by a predetermined amount.

Figure 25:
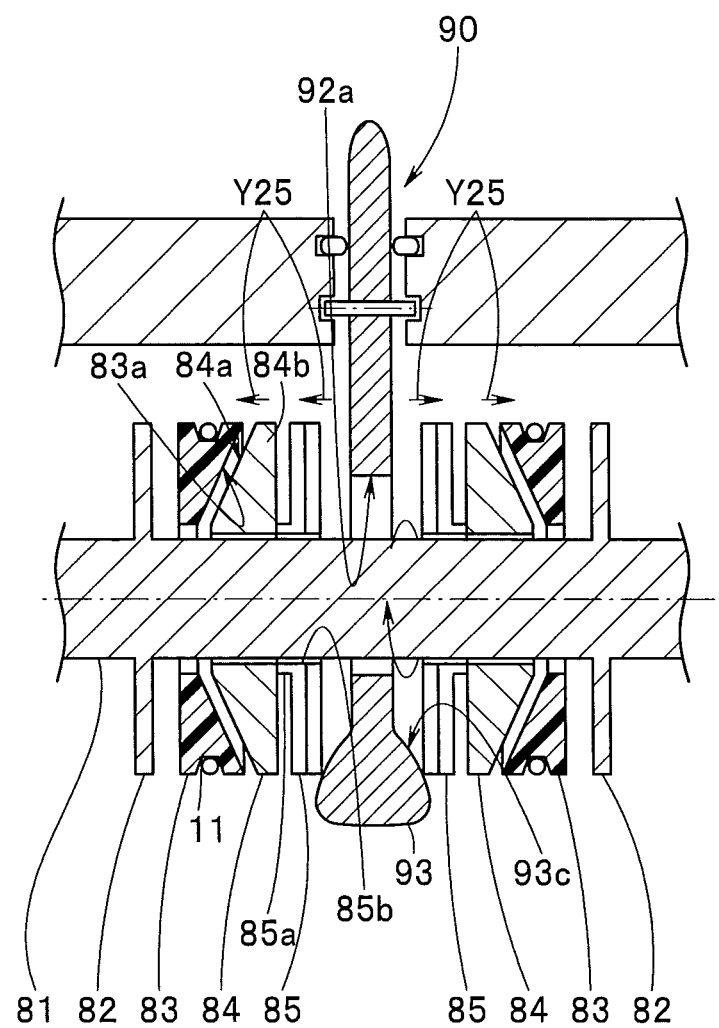

Then, as illustrated in FIG. 25, as a result of the inclined cam surface 93c being brought close to the pulley shaft center, the inclined cam surface 93c moves the pressing members 85 in the arrow Y25 direction. Then, the pressing portions 85a of the pressing members 85 press the flat side faces 84b of the contact resistance changing members 84. Then, the contact resistance changing members 84 are moved in the arrow Y25 directions. Upon the movement of the contact resistance changing members 84, the projecting inclination side faces 84a are brought close to the recess inclination side faces 83a of the rotating bodies 83.

Here, the operator performs a tilting operation of the manipulator 5 again. Then, along with the tilting operation, the rotating bodies 83 are elastically deformed to bring the recess inclination side faces 83a of the rotating bodies 83 into contact with the projecting inclination side faces 84a of the contact resistance changing members 84, whereby a friction force is generated. Thus, a light operational feeling can be obtained compared to that before movement of the operation lever 90.

If an even lighter operational feeling is demanded, the operation lever 90 is further operated to bring the inclined cam surface 93c further close to the pulley shaft center. Consequently, as described above, the inclined cam surface 93c moves the pressing members 85 in the arrow Y25 directions. Then, the pressing portions 85a of the pressing members 85 press the flat side faces 84b of the contact resistance changing members 84, whereby the contact resistance changing members 84 are moved in the arrow Y25 direction, and the projecting inclination side faces 84a of the contact resistance changing members 84 are arranged further close to the recess inclination side faces 83a of the rotating bodies 83.

As a result, when the operator performs a tilting operation of the manipulator 5 again, along with the tilting operation, the rotating bodies 83 are elastically deformed, whereby the area of contact between the recess inclination side face 83a of each rotating body 83 and the projecting inclination side face 84a of the corresponding contact resistance changing member 84 increases, resulting in generation of a still larger friction force.

As described above, the operation lever 90 is operated to bring the inclined cam surface 93c close to the pulley shaft center, whereby the inclined cam surface 93c is made to abut the pressing members 85. Then, along with the movement of the inclined cam surface 93c, the pressing members 85 and the contact resistance changing members 84 move along the pulley shaft 81. Then, the projecting inclination side faces 84a of the contact resistance changing members 84 are arranged on the recess inclination side faces 83a of the rotating bodies 83 to change a friction force generated between the rotating body 83 and the contact resistance changing member 84, enabling adjustment of the assist force amount.

Also, a configuration in which the bearing portions 85b are provided in the pressing members 85 to make the pressing members 85 slide relative to the pulley shaft 81 is employed. As a result, during rotation of the pulley shaft 81, the friction force can be changed by operating the operation lever 90 to adjust positions of the contact resistance changing members 84, enabling enhancement in operability. In addition, each pressing member 85 includes the bearing portion 85b. As a result, it is possible to prevent occurrence of a problem in feeling during operation of the operation lever 90 as a result of, when a friction force is generated between a rotating body 83 and a corresponding contact resistance changing member 84, a force of rotation of the pulley shaft 81 being transmitted to the operation lever 90.

Note that the pulley 20F according to the present embodiment is configured so that a pair of rotating bodies 83 are arranged on one pulley shaft 81. In other words, only either wires for upper and lower directions or wires for left-hand and right-hand directions are wound on the pair of rotating bodies 83 on the pulley 20F. In other words, if a bending portion of an endoscope bends upward, downward, leftward and rightward, a pair of pulleys 20F are disposed in parallel in an operation portion.

The present invention is not limited only to the above-described embodiments and various modifications are possible without departing from the spirit of the invention.

What is claimed is:
1. An endoscope comprising:
an operation portion provided on a proximal end side of an insertion portion that includes a distal end portion including an image pickup device that picks up an image of an object, a bendable bending portion including a plurality of bending pieces continuously provided and a flexible tube portion that is elongated and has flexibility, the distal end portion, the bending portion and the flexible tube portion being continuously provided;
a plurality of pairs of pulling members that each extend from the bending pieces included in the bending portion, are guided into the operation portion and bend the bending portion by a relative movement;
a pulley provided inside the operation portion, the pulley being rotated by a motor provided in the operation portion in a pulling direction in which any of the pulling members is pulled;
a plurality of rotating bodies that are elastically deformable and have outer circumferential faces on which respective one of the plurality of pairs of pulling members are respectively wound and arranged, the plurality of rotating bodies being arranged in a loose-fit state on an outer circumferential face side of the pulley;
a suspension frame including attachment portions to which proximal end portions of the plurality of pairs of pulling members guided into the operation portion are respectively fixed;
a manipulator that is provided so as to project from a surface of the operation portion and includes a shaft portion capable of being subjected to a tilting operation, the suspension frame being provided at the shaft portion of the manipulator, the attachment portions of the suspension frame being provided at positions facing each other across the manipulator, the manipulator being capable of applying an amount of force of pulling a part of a pulling member on the insertion portion side relative to the pulley in the pulling direction using a frictional resistance generated as a result of, upon an operation to tilt the manipulator being performed, a part of the pulling member on the manipulator side relative to the pulley being pulled to reduce a diameter of the corresponding rotating body and an inner surface of the rotating body being thereby brought into contact with an outer circumferential face of the pulley rotated by the motor; and a force amount adjustment section capable of changing an amount of force of the operation to tilt the manipulator, the force amount adjustment section reducing slippage of the rotating body relative to the pulley, when the operation is performed to increase a bending angle of the bending portion with an increase of a tilting angle of the manipulator, by adjusting a friction generation state in which the frictional resistance is generated by increasing a rotation speed of the motor and thereby increasing an area of contact between the rotating body and the pulley to increase a contact resistance between the outer circumferential face of the pulley and the inner surface of the rotating body.

2. The endoscope according to claim 1, wherein the force amount adjustment section increases the rotation speed of the motor according to a tilting angle of the shaft portion.

3. The endoscope according to claim 2, wherein the bending control apparatus includes a change/setting switch that changes a rotation speed in an initial state of the motor.

4. The endoscope according to claim 2,
wherein in a configuration in which a plurality of pieces of table data are registered in the storage section,
the bending control apparatus includes a selection switch for selecting one piece of table data from the plurality of pieces of table data registered in the storage section.

5. The endoscope according to claim 2, wherein if a range of fluctuations of a value of current flowing in the motor remains within a threshold range stored in the storage section for a certain time period or longer, the rotation frequency of the motor is increased.

6. The endoscope according to claim 2, wherein if a range of fluctuations of the tilting angle of the manipulator remains within a threshold range stored in the storage section for a certain time period or longer, the rotation frequency of the motor is increased.

7. The endoscope according to claim 1,
wherein the force amount adjustment section includes:
a tilting operation angle detection apparatus that detects a tilting operation angle of the shaft portion of the manipulator and a motor rotation state detection apparatus that detects a rotation frequency or the rotation speed of the motor, the tilting operation angle detection apparatus and the motor rotation state detection apparatus being included in the operation portion; and
a storage section with table data registered therein, a relationship between a tilting angle of the shaft portion of the manipulator and a motor rotation speed corresponding to the tilting angle being set in the table data, a comparison section to which the tilting angle of the shaft portion detected by the tilting operation angle detection apparatus and the rotation frequency or the rotation speed detected by the motor rotation state detection apparatus are inputted, the comparison section making a comparison with the table data registered in the storage section and outputting a result of the comparison as motor control information, and a control section that controls the rotation frequency of the motor based on the motor control information inputted from the comparison section, the storage section, the comparison section and the control section being included in a bending control apparatus that is an apparatus external to the endoscope.

8. The endoscope according to claim 1, wherein the motor is a single motor and the pulley is a single pulley rotated by the single motor and the plurality of rotating bodies being arranged in a loose-fit state on the outer circumferential face side of the single pulley.

* * * * *